(12) United States Patent
Damani et al.

(10) Patent No.: US 9,852,266 B2
(45) Date of Patent: Dec. 26, 2017

(54) INTERACTIVE GRAPHICAL USER INTERFACES FOR IMPLEMENTING PERSONALIZED HEALTH AND WELLNESS PROGRAMS

(71) Applicant: MD REVOLUTION, INC., San Diego, CA (US)

(72) Inventors: Samir B. Damani, San Diego, CA (US); Vincent Valentino, San Diego, CA (US); Pratik Patel, Hawthorn Woods, IL (US)

(73) Assignee: MD REVOLUTION, INC., San Diego, CA (US)

(*) Notice: Subject to any disclaimer, the term of this patent is extended or adjusted under 35 U.S.C. 154(b) by 0 days.

(21) Appl. No.: 14/034,508

(22) Filed: Sep. 23, 2013

(65) Prior Publication Data

US 2014/0089836 A1    Mar. 27, 2014

Related U.S. Application Data

(60) Provisional application No. 61/704,415, filed on Sep. 21, 2012, provisional application No. 61/722,774, filed on Nov. 5, 2012.

(51) Int. Cl.
*G06F 3/048*      (2013.01)
*G06F 19/00*     (2011.01)
(Continued)

(52) U.S. Cl.
CPC ........ *G06F 19/3431* (2013.01); *G06F 19/322* (2013.01); *G06F 19/324* (2013.01);
(Continued)

(58) Field of Classification Search
CPC combination set(s) only.
See application file for complete search history.

(56) References Cited

U.S. PATENT DOCUMENTS

| 8,784,209 B2 * | 7/2014 | Oswald | A63B 24/0062 |
| | | | 434/247 |
| 2003/0204412 A1 * | 10/2003 | Brier | G06F 19/3475 |
| | | | 705/2 |

(Continued)

FOREIGN PATENT DOCUMENTS

| KR | 1020030062728 A1 | 7/2003 |
| KR | 1020050050768 A1 | 6/2005 |

OTHER PUBLICATIONS

Oh, Eung Gie, Authorized Officer, Korean Intellectual Property Office, in PCT Application No. PCT/US13/61207, in International Search Report and Written Opinion, dated Jan. 9, 2014, 13 pages.

*Primary Examiner* — Hien Duong
(74) *Attorney, Agent, or Firm* — Procopio, Cory, Hargreaves & Savitch LLP

(57) ABSTRACT

User-specific medical, genetic, fitness, environmental and nutritional data is collected to develop personalized health and wellness programs for improving a user's health and wellness. The user-specific data may be collected from medical or genetic tests, mobile health devices worn by the user and applications through which the user manually inputs information. The user-specific data is then collected and analyzed together based on knowledge of the interrelationships between medical, genetic, fitness, environmental and nutrition data to develop a comprehensive user profile and personalized health and wellness programs that are targeted to improving specific areas of the user's health by implementing changes in fitness, nutrition, medical treatment, environment, etc. The user is provided with a customizable, interactive dashboard graphical user interface of their current health and wellness data, which, along with notifications, incentives and rewards, helps the user improve their overall health and wellness and significantly reduce their risk of morbidity.

24 Claims, 37 Drawing Sheets

(51) Int. Cl.
  *G06Q 10/10* (2012.01)
  *G06Q 50/22* (2012.01)

(52) U.S. Cl.
  CPC ...... *G06F 19/3406* (2013.01); *G06F 19/3418* (2013.01); *G06F 19/3475* (2013.01); *G06F 19/3481* (2013.01); *G06F 19/3487* (2013.01); *G06Q 10/10* (2013.01); *G06Q 50/22* (2013.01)

(56) References Cited

U.S. PATENT DOCUMENTS

| | | | |
|---|---|---|---|
| 2004/0198555 A1* | 10/2004 | Anderson | A63B 24/00 482/8 |
| 2006/0205564 A1* | 9/2006 | Peterson | A63B 69/00 482/8 |
| 2006/0287883 A1* | 12/2006 | Turgiss et al. | 705/2 |
| 2007/0203753 A1* | 8/2007 | Hasan | G06F 19/322 705/3 |
| 2007/0225614 A1* | 9/2007 | Naghavi et al. | 600/549 |
| 2008/0246629 A1* | 10/2008 | Tsui et al. | 340/870.07 |
| 2008/0255873 A1 | 10/2008 | Berkley | |
| 2009/0132284 A1* | 5/2009 | Fey | G06F 19/322 705/3 |
| 2010/0228561 A1* | 9/2010 | Boyce et al. | 705/2 |
| 2012/0040799 A1* | 2/2012 | Jaquish et al. | 482/9 |
| 2012/0046966 A1* | 2/2012 | Chang et al. | 705/3 |
| 2012/0059230 A1 | 3/2012 | Teller et al. | |
| 2012/0059664 A1* | 3/2012 | Georgiev et al. | 705/2 |
| 2012/0083669 A1* | 4/2012 | Abujbara | G06F 19/3475 600/300 |
| 2012/0130732 A1* | 5/2012 | Blander | G06Q 50/22 705/2 |
| 2012/0185282 A1* | 7/2012 | Gore et al. | 705/4 |
| 2012/0191469 A1* | 7/2012 | Akradi | G06Q 50/22 705/2 |
| 2012/0244504 A1* | 9/2012 | Wasserman | G09B 19/00 434/238 |
| 2012/0251993 A1* | 10/2012 | Chidambaran et al. | 434/362 |
| 2012/0308975 A1* | 12/2012 | Hsiao et al. | 434/247 |
| 2012/0313776 A1* | 12/2012 | Utter, II | 340/539.12 |
| 2013/0004923 A1* | 1/2013 | Utter, II | G06F 19/3475 434/127 |
| 2013/0013331 A1* | 1/2013 | Horseman | G06F 19/3418 705/2 |
| 2013/0096953 A1* | 4/2013 | Beverly et al. | 705/3 |
| 2013/0191141 A1* | 7/2013 | Chun | G06Q 50/22 705/2 |
| 2013/0211858 A1* | 8/2013 | Ohnemus | G06F 19/322 705/3 |
| 2013/0337974 A1* | 12/2013 | Yanev | G06F 19/3481 482/8 |
| 2014/0052458 A1* | 2/2014 | Ghazvini et al. | 705/2 |
| 2014/0106312 A1* | 4/2014 | Klein | G06F 19/3475 434/127 |
| 2014/0107932 A1* | 4/2014 | Luna | G01D 21/00 702/19 |
| 2014/0302470 A1* | 10/2014 | Zapantis | G09B 19/00 434/236 |

\* cited by examiner

Name _____ DOB _____ WT _____

Protocol 3.0mph top speed- change workload at the beginning of each stage

| Stage-Time | Workload Speed/incline | VO2 ml/kg/min | Record HR @ AT and Peak bpm |
|---|---|---|---|
| 0:00-1:00 ⟶ 802 | 2.5 / 0 ⟶ 804 | 14.7 ⟶ 806 | _____ ⟶ 808 |
| 1:00-3:00 | 3.0 / 0 | 17.1 | _____ |
| 3:00-4:00 | 3.0 / 1 | 17.7 | _____ |
| 4:00-4:30 | 3.0 / 2 | 18.3 | _____ |
| 4:30-5:00 | 3.0 / 3 | 18.9 | _____ |
| 5:00-5:30 | 3.0 / 4 | 19.6 | _____ |
| 5:30-6:00 | 3.0 / 5 | 20.2 | _____ |
| 6:00-6:30 | 3.0 / 6 | 20.8 | _____ |
| 6:30-7:00 | 3.0 / 7 | 21.4 | _____ |
| 7:00-7:30 | 3.0 / 8 | 22.1 | _____ |
| 7:30-8:00 | 3.0 / 9 | 22.7 | _____ |
| 8:00-8:30 | 3.0 / 10 | 23.3 | _____ |
| 8:30-9:00 | 3.2 / 10 | 24.7 | _____ |
| 9:00-9:30 | 3.5 / 10 | 26.7 | _____ |
| 9:30-10:00 | 3.7 / 10 | 28.0 | _____ |
| 10:00-10:30 | 4.0 / 10 | 30.1 | _____ |

⟵ 810

Record 2:00 HR recovery after the final stage is completeed during the test    2:00 HR recovery _____

FIG. 8A

Name _____ DOB _____ WT _____

Protocol  10.0mph top speed- change workload at the beginning of each stage

| Stage-Time | Workload Speed/incline | VO2 ml/kg/min | Record HR @ AT and Peak bpm |
|---|---|---|---|
| 0:00-1:00 | 3.0 / 0 | 17.1 | _____ |
| 1:00-2:00 | 4.0 / 0 | 21.7 | _____ |
| 2:00-3:00 | 5.0 / 0 | 26.3 | _____ |
| 3:00-4:00 | 6.0 / 0 | 31.0 | _____ |
| 4:00-4:30 | 7.0 / 0 | 35.6 | _____ |
| 4:30-5:00 | 8.0 / 0 | 40.3 | _____ |
| 5:00-5:30 | 9.0 / 0 | 44.9 | _____ |
| 5:30-6:00 | 9.5 / 0 | 47.3 | _____ |
| 6:00-6:30 | 10.0 / 0 | 49.6 | _____ |
| 6:30-7:00 | 10.0 / 1 | 51.7 | _____ |
| 7:00-7:30 | 10.0 / 2 | 53.8 | _____ |
| 7:30-8:00 | 10.0 / 3 | 55.9 | _____ |
| 8:00-8:30 | 10.0 / 4 | 57.9 | _____ |
| 8:30-9:00 | 10.0 / 5 | 60.0 | _____ |
| 9:00-9:30 | 10.0 / 6 | 62.1 | _____ |
| 9:30-10:00 | 10.0 / 7 | 64.2 | _____ |
| 10:00-10:30 | 10.0 / 8 | 66.3 | _____ |
| 10:30-11:00 | 10.0 / 9 | 68.4 | _____ |
| 11:00-11:30 | 10.0 / 10 | 70.5 | _____ |
| 11:30-12:00 | 10.2 / 10 | 71.8 | _____ |
| 11:00-11:30 | 10.5 / 10 | 73.9 | _____ |
| 11:30-12:00 | 10.7 / 10 | 75.2 | _____ |
| 12:00-12:30 | 11.0 / 10 | 77.2 | _____ |

Labels: 804 (Workload column), 806 (VO2 column), 808 (HR column)

Record 2:00 HR recovery after the final stage is completed during the test.  2:00 HR recovery _____

FIG. 8B

Points System

| Activity | Value | Group A | Group B | Group C | Threshold |
|---|---|---|---|---|---|
| Record # of Steps (Fitbit) | 1 point / day | ✓ | | | 3 days a week = 55 pts |
| 7500 Steps per Day (Fitbit) | 5 points / day | ✓ | ✓ | ✓ | 3 days a week = 165 pts |
| 2x Very Active Minutes (Fitbit) | 5 points / day | ✓ | ✓ | ✓ | 3 days a week = 165 pts |
| Record Weight (Withings or Manual) | 1 point / day | ✓ | ✓ | ✓ | 2 days a week = 22 pts |
| Post Meal Nutritional Pic | 2.5 points / day | | ✓ | ✓ | 3 days a week = 105 pts |
| Step Achievements (ex. Vegas to Hollywood) | Incremental by 5 points / landmark | ✓ | ✓ | ✓ | 225 total for program |
| | | | | | 750 Core Program Points |

FIG. 25

Outcomes Based Points

| Based on Assessments | | | | | | |
|---|---|---|---|---|---|---|
| Criteria | Value | Group 1 | Group 2 | Group 3 | Group 4 |
| RMR % to Goal | % of 250 points | ✓ | ✓ | | ✓ |
| Visceral Fat % to Goal | % of 250 points | ✓ | ✓ | ✓ | ✓ |
| Body Fat % to Goal | % of 250 points | ✓ | ✓ | ✓ | |
| VO₂ % to Goal | % of 250 points | ✓ | ✓ | ✓ | ✓ |
| HbA1c % to Goal | % of 250 points | ✓ | ✓ | ✓ | ✓ |

FIG. 26

Examples of Incentive Design

| Design | Sharp Incentive | MDR Incentive | Kicker |
|---|---|---|---|
| Group A | Individual | Devices | Exercise Equipment | Awards for Top Improvers and Point Gainers |
| Group B | Individual | Devices | Exercise Equipment | |
| Group C | | | Exercise Equipment | |

FIG. 27

Additional Points

| Activity | Value | Group A | Group B | Group C | Threshold |
|---|---|---|---|---|---|
| Log Blood Pressure | 5 points | ✓ | ✓ | Manual entry | Once / month |
| 100+ Very Active Minutes / Week (Fitbit) | 25 points | ✓ | ✓ | ✓ | |
| Record Resistance Training (Fitbit) | 5 points | ✓ | ✓ | ✓ | 2x per week |
| Blood Glucose Reading | 5 points | ✓ | ✓ | Manual entry | n/a |
| Sleep (avg hours over 3 days) (Fitbit) | 5 points | ✓ | ✓ | ✓ | |
| 90 mins of Exercise over 3 Days (5x/mi) | 25 points | ✓ | ✓ | ✓ | |

FIG. 28

| Change in | # of Patients | Average | 95% CI | P-value | Male | Female | P-value |
|---|---|---|---|---|---|---|---|
| Weight | 90 | -4.64 | -6.18, -3.09 | $4.8 \times 10^{-8}$ | -3.91 | -5.08 | ns |
| Body Mass Index | 90 | -0.67 | -0.90, -0.45 | $3. \times 10^{-8}$ | -0.61 | -0.71 | ns |
| Body Fat | 90 | -1.39 | -1.93, -0.84 | $2.3 \times 10^{-6}$ | -1.12 | -1.56 | ns |
| Trunk Fat | 90 | -2.29 | -3.90, -1.49 | $1.8 \times 10^{-7}$ | -1.81 | -2.61 | ns |
| Resting Metabolic Rate | 90 | 0.22 | 0.13, 0.31 | $5.9 \times 10^{-6}$ | 0.29 | 0.17 | ns |
| Oxygen Consumption ($vO^2$) | 88 | 4.74 | 3.90, 5.55 | $2.2 \times 10^{-16}$ | 3.76 | 5.35 | 0.054 |

FIG. 29

INTERACTIVE GRAPHICAL USER INTERFACES FOR IMPLEMENTING PERSONALIZED HEALTH AND WELLNESS PROGRAMS

BACKGROUND

1. Technical Field

The embodiments described herein are related to interactive mobile health devices and applications, and more particularly to an interactive dashboard graphical user interface which collects health information for a user, displays a personalized health and wellness program, tracks the user's activity using the mobile health devices and applications and provides notifications, rewards and incentives to the user for participation in the health and wellness program.

2. Related Art

A person's overall health and wellness is the result of a number of different factors. Genetic profiles, medical history, fitness activity and nutrition all affect a person's overall health and wellness. The interrelationships between all of these factors are still not fully understood and are the subject of continuing research. However, even for factors which are individually known to be the cause of disease or promote health and wellness, there is no mechanism for a person or even a healthcare provider to attempt to understand these factors, how they relate to each other and how they may be utilized in optimizing a person's overall health and wellness.

Cardiac disease is the leading cause of death, and has been since 1918. Someone has a heart attack or stroke every 10 seconds, amounting to 2,400,000 deaths in the United States each year. 1 in 3 adults in the U.S. will die from cardiovascular disease, and not surprisingly, 1 in 3 adults in the U.S. are obese. 1 in 3 people also have undiagnosed cardiovascular disease, and cancer and heart disease combine for over half of the deaths in the U.S. each year. The traditional methods of treating cardiovascular disease are not driving down mortality, and studies are beginning to show an "obesity paradox" based on the lack of correlation between adiposity and cardiovascular disease. FIG. 1 is a bar graph illustrating a comparison between body mass index (BMI) and central obesity (via waist-to-hip ratio) in assessing mortality of subjects with coronary artery disease. As shown in FIG. 1, the highest mortality rates are found in individuals with a waist-to-hip ratio of greater than 1, indicating a large amount of visceral fat surrounding the abdominal organs. The mortality rate is even higher amongst the individuals with a waist-to-hip ratio greater than 1 who have an overall low BMI of 18.5-21.9, indicating that an individual with a low BMI and a concentration of fat only around the waist are the most at-risk individuals.

FIG. 2 further illustrates this statistic via the body-shape illustrations of the individuals represented in the bar graph of FIG. 1. As stated below the illustrations, the increased risk of mortality of Person 2 (the individual with a lower BMI but a high waist-to-hip ratio) is statistically significant in comparison with the other individuals, including Person 5, who would be classified as morbidly obese. Additional recent studies have also noted the unusual lack of correlation between BMI and morbidity, once thought to be the primary measurement indicative of health, likelihood of disease and overall morbidity.

Existing methods of promoting weight loss, better diet and regular exercise fail to account for the peculiarities of the obesity paradox, and are therefore failing to address the root cause of morbidity for a large population of individuals which are at risk of cardiovascular disease.

SUMMARY

The embodiments described herein relate to interactive graphical user interfaces for implementing personalized health and wellness programs. User-specific medical, genetic, fitness, environmental and nutritional data are collected and analyzed to develop comprehensive, personalized health and wellness programs for improving key health factors which have a high correlation to common morbidities. The user-specific data may be collected from a variety of sources, including medical or genetic tests, mobile health devices worn by the user and applications through which the user manually inputs information. The user-specific data is then analyzed based on knowledge of the interrelationships between medical, genetic, fitness, environmental and nutrition data to develop a comprehensive user profile. The user profile is then used to develop personalized health and wellness programs that are targeted to improving key health factors such as oxygen consumption, metabolism, visceral fat, body fat and posture, amongst others, by implementing changes in fitness, nutrition, health care, environment and other behavioral components. The user is provided with a customized, interactive graphical user interface dashboard and one or more mobile health devices and applications to track and monitor their current health and wellness data, communicate with administrators, healthcare professionals and other users, and utilize points and reward programs to motivate the user to achieve their personalized goals.

BRIEF DESCRIPTION OF THE DRAWINGS

The accompanying drawings, which are incorporated in and constitute a part of the specification, illustrate embodiments of the invention and, together with the description, serve to explain the objects, advantages, and principles of the invention. In the drawings:

FIGS. 8A and 8B illustrate a chart utilized for measuring beats per minute while assessing the user's maximum heart rate;

FIG. 25 is a table illustrating a points reward system, according to one embodiment of the invention;

FIG. 26 is another table illustrating an outcomes-based points reward system, according to one embodiment of the invention;

FIG. 27 is a further table illustrating an incentives-based points reward system, according to one embodiment of the invention;

FIG. 28 is an yet further table illustrating additional points rewards, according to one embodiment of the invention;

FIG. 29 is a table illustrating physiological changes in a set of patients over a period of time after using the systems and methods described herein, according to one embodiment of the invention;

DETAILED DESCRIPTION

Figure 1:
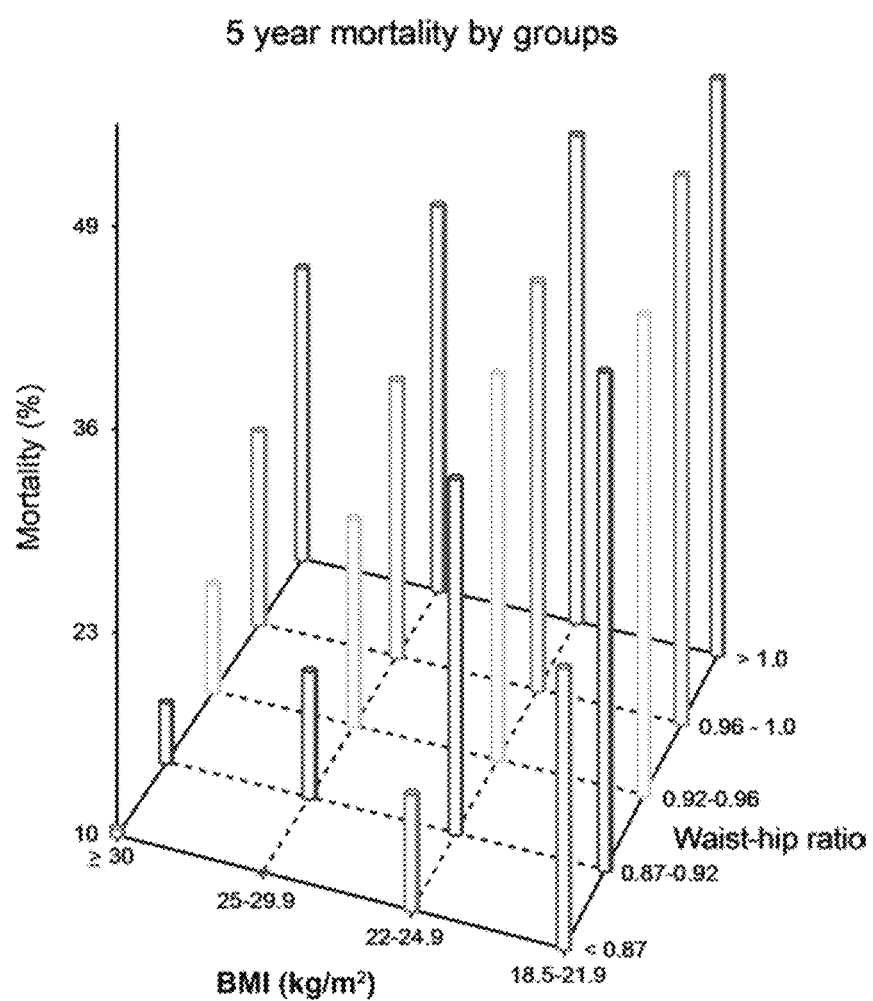
FIG. 1 is a bar graph illustrating a correlation between body mass index, central obesity and morbidity.
Figure 2:
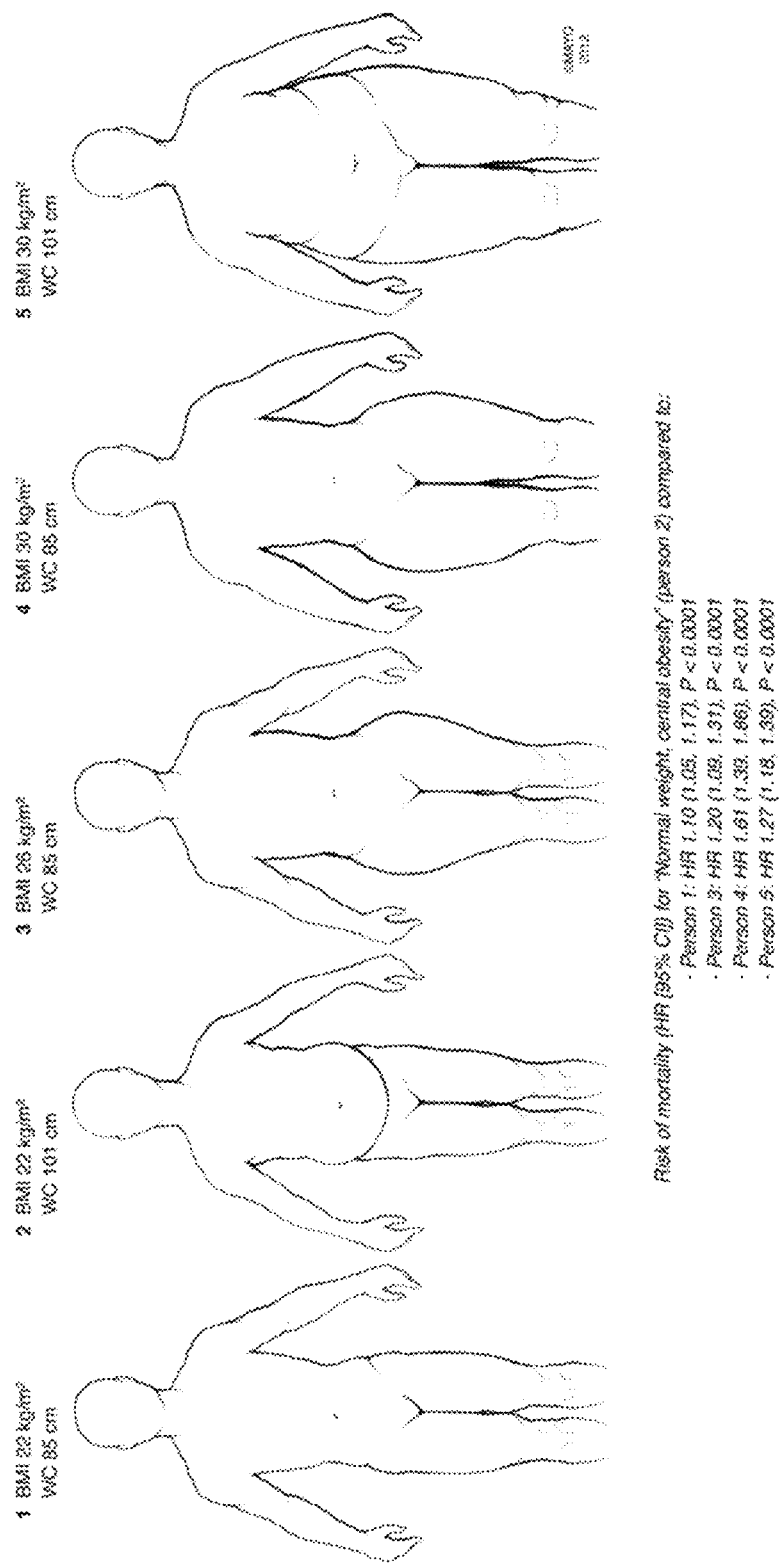
FIG. 2 is an illustration of different body types based on body mass index and central obesity as they relate to morbidity.

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation. As such, this detailed description of various alternative embodiments should not be construed to limit the scope or breadth of the present invention as set forth below.

The embodiments described herein relate to collecting and analyzing user-specific medical, genetic, fitness, environmental and nutritional data to develop comprehensive, personalized health and wellness programs for improving key health factors which have a high correlation to common morbidities. The user-specific data may be collected from a variety of sources, including traditional medicine, genetic testing, lab testing, nutrition information, fitness, metabolic testing, mobile health devices worn by the user and applications through which the user manually inputs information. The user-specific data is then collected and analyzed together based on knowledge of the interrelationships between medical, genetic, fitness, environmental and nutrition data to develop a comprehensive user profile. The user profile is then used to develop personalized health and wellness programs that are targeted to improving key health factors such as oxygen consumption ($VO_2$), metabolism, visceral fat, body fat and posture, amongst others, by implementing changes in the user's fitness, nutrition, health care, environment and other behavioral components. The user is provided with a customized, interactive graphical user interface dashboard and one or more mobile health devices and applications to track and monitor their current health and wellness data and motivate the user to achieve their personalized goals. The dashboard provides notifications and alerts, points and rewards and analytics of user and group data which can be viewed by the user, a healthcare professional or healthcare plan administrator to monitor and adjust the programs to obtain optimal results.

The systems and methods described herein utilize mobile health technology and analytics to develop comprehensive health and wellness programs customized for each user based on understandings of the interrelationship between medical, genetic, fitness, environmental and nutrition data. By leveraging the same mobile health technology which collects the initial data to continually monitor multiple aspects of the user's health, the user's progress in implementing the health and wellness programs can be easily monitored and adjusted based on their progress to optimize their goals.

The health and wellness programs described herein are designed to create statistically significant changes in key health factors—such as oxygen consumption, resting metabolic rate and visceral fat—which have high correlations with reductions in leading morbidities and lead to greater improvements in the user's overall health and wellness.

I. System Overview

Figure 3:
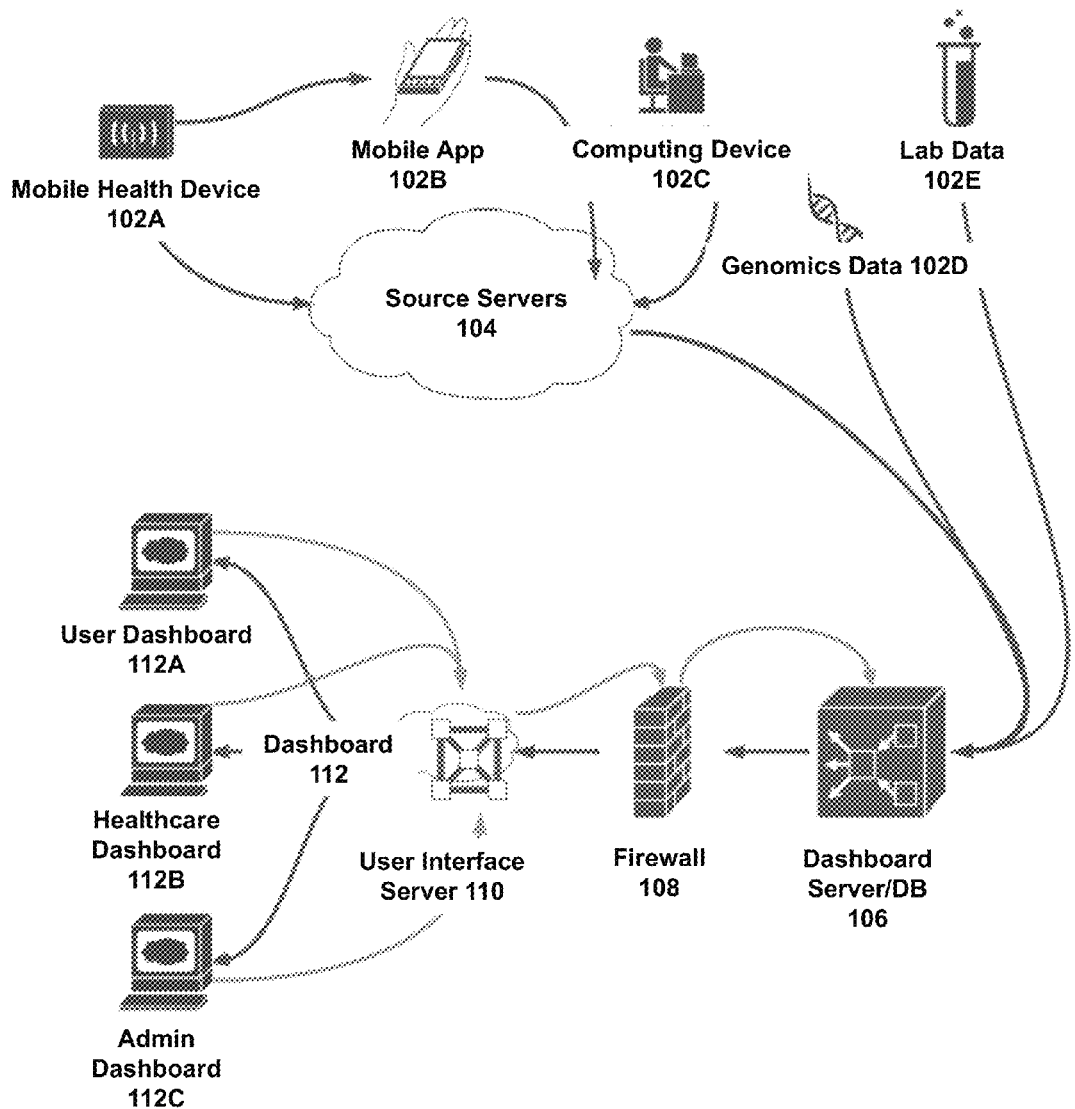
FIG. 3 is a diagram illustrating a system and method of collecting and analyzing user-specific data to develop comprehensive, personalized health and wellness programs, according to one embodiment of the invention.

FIG. 3 illustrates one embodiment of a system 100 of collecting and analyzing user-specific data to develop comprehensive personalized health and wellness programs. In this embodiment, data on a user is collected from a plurality of sources 102, such as a mobile health device 102A, a mobile application on a portable electronic device 102B or through manual user entry 102C via a computing device. The mobile health devices and mobile applications may be configured to collect information on the user as the user wears or uses the device. In one embodiment, these devices may communicate with one or more source servers 104, such as device or application servers that receive data collected and then communicate with a dashboard server 106 of a front-end cloud server to collect the data for analysis. In addition to the devices, additional user data may be collected at the dashboard database in the form of genomic data 102D from a genomic report or lab results 102E from lab tests that the user has undergone. Additional data may be entered manually by the user, the user's physician, fitness trainer or other health and wellness professional by a computing device, as illustrated in 102C. The dashboard server and database 106 will collect and store all of the medical, genetic, fitness, environmental and nutrition information about the user that will then be analyzed to generate a user profile.

The mobile health devices 102A may be configured to continually collect and report data to the dashboard database in real-time or at periodic increments so the user profile can be continually updated to provide the most relevant information about the user's health and wellness. The mobile health devices may be connected to a network and configured to wirelessly transmit data to the dashboard server and database 106 or through a device-specific or application-specific server such as the source server 104. Some devices may require user input, such as a nutrition application running on a portable electronic device in which the user inputs dietary and nutrition information. The user may be responsible for submitting the data manually as it is entered or at periodic time periods after a certain amount of data is collected. In some embodiments, the nutrition data may be obtained from mobile health devices or at least more accurately tracked by software or applications running on the portable electronic device 102B (such as a tablet or smartphone). Similarly, some user fitness data may be generated or reported by a user.

Once the user data is collected at the dashboard database, the dashboard server 106 will use the data in order to analyze the data and generate a user profile. In this embodiment, the data in the dashboard server and database 106 is protected by a secure firewall 108, and additional firewalls may be placed throughout the system to protect data being transmitted across the system. The dashboard server 106 then analyzes the data using customized algorithms which leverage understandings of the relationships between the medical, genetic, fitness, environmental and nutrition data in order to generate a user profile.

The user profile is then used to generate at least one health and wellness program at the dashboard server 106 which contains recommendations for the user specific to their medical health, fitness, nutrition and environment. The recommendations may relate to recommended user activity such as exercise, behavioral changes related to their environment (such as sleep), or nutrition recommendations related to their diet. In addition, the recommendations may relate to achieving desired physiological measurements of visceral fat, resting metabolic rate, body fat, posture, cholesterol, blood pressure, body mass, etc.

The user profile and health and wellness programs may be displayed to a user on a graphical user interface (GUI) in the form of a dashboard 112 of information which provides an interactive, visual summary of the user's health and wellness as compiled and analyzed by the dashboard server 106. Once the dashboard is generated, it may be customized and transmitted to one or more destination devices for display to an interested party, including the user dashboard 112A (patient), a healthcare team dashboard 112B for healthcare professionals responsible for the user's health, or a corporate wellness dashboard 112C for an administrator set up to monitor the user's progress toward specific health goals. The users, healthcare professionals and administrators may interact with the dashboard through a user interface server 110 which will communicate with the dashboard server and database 106.

The mobile health devices 102A and other applications 102B will continue to be utilized to report new user data once the user has begun to implement the health and wellness programs, and this new data can then be used by the dashboard server 106 to compare with the original user data to determine if the user is implementing the health and wellness programs and achieving improved health and wellness through the implementation of the programs. The new and original data may be displayed on the dashboard 112 in graphical or other visual forms to help the user or a health professional easily view the user's progress toward one or more goals related to the health and wellness programs. By obtaining continuous feedback from the user, the health and wellness programs may be continually modified.

Figure 4:
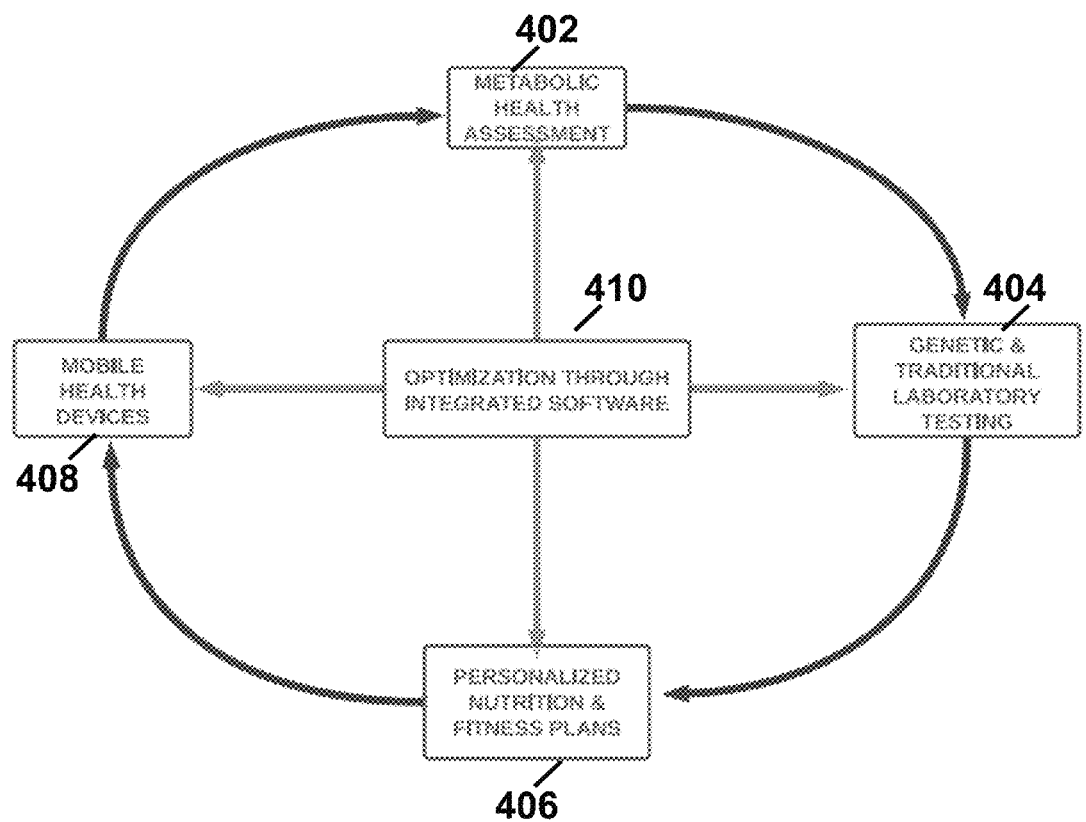
FIG. 4 is a block diagram illustrating the relationship between sources of user-specific data and how they are utilizes to develop the personalized health and wellness programs, according to one embodiment, the results of which are reflected in the health and wellness dashboard.
Figure 5:
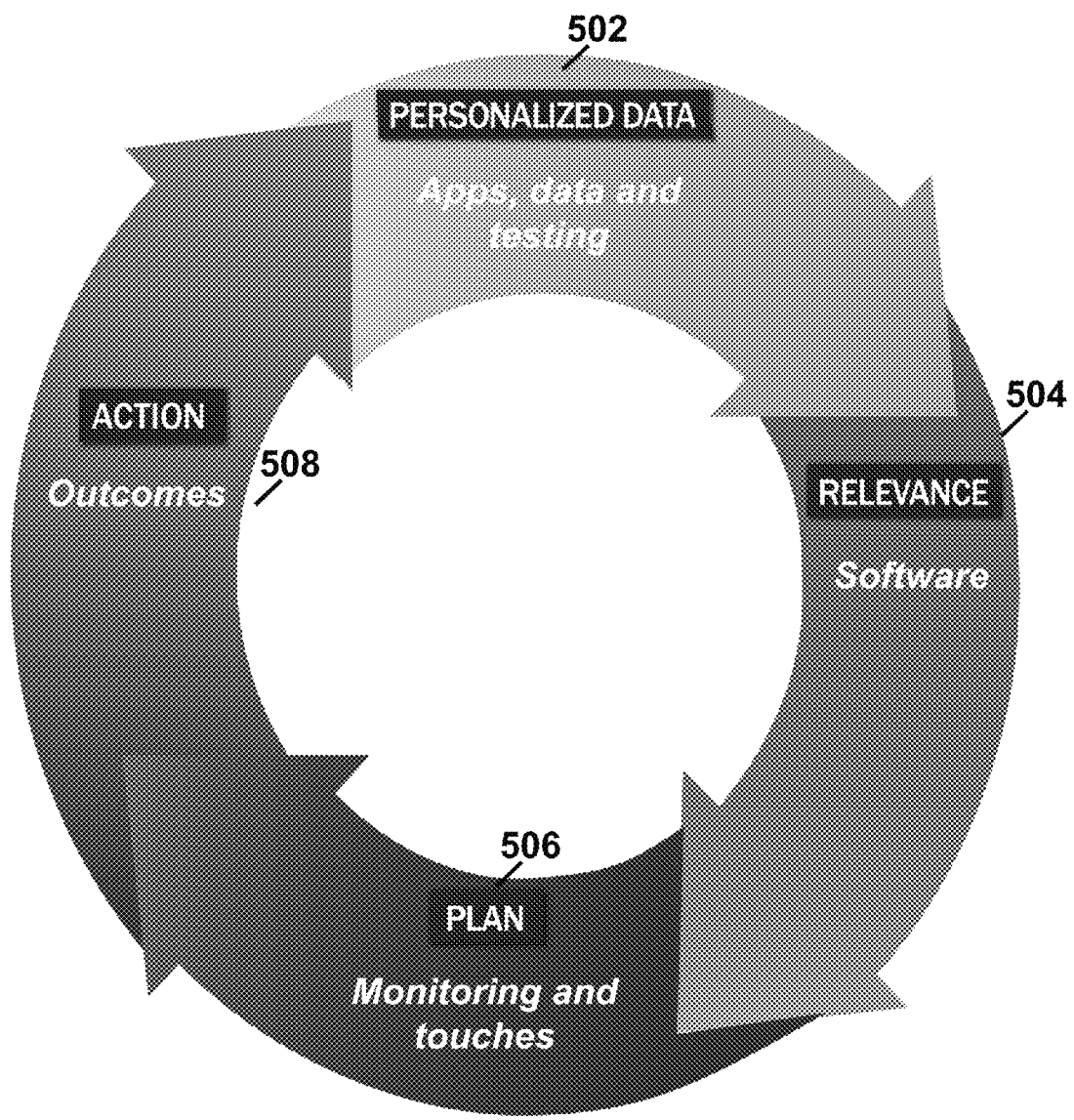
FIG. 5 is a flow diagram illustrating the relationship of personalized data with software to derive plans that drive outcomes, according to one embodiment of the invention.

FIG. 4 is a graphical illustration of the relationships between sources of user-specific data and how they are utilizes to develop the personalized health and wellness programs. The metabolic health assessment 402, genetic and traditional lab testing 404, personalized nutrition and fitness plans 406 and mobile health devices 408 all operate through optimization of integrated software 410 at the system level to improve the overall health and wellness of the user. Additional details of these relationships will be provided further herein. FIG. 5 is a flow diagram illustrating the relationships of personalized data 502 with software 504 to derive plans 506 that drive outcomes 508. The software 504 obtains the personalized data 502 from the user through the user assessments, then develops the personalized plans 506 for the user to implement. The plans 506 are then monitored and evaluated through the mobile health devices connected with the user and the dashboard interface, all of which drive positive outcomes 508 for the user in terms of reduced morbidity and improved health and wellness, improving the user's personalized data 502.

II. Program Steps

Figure 6:
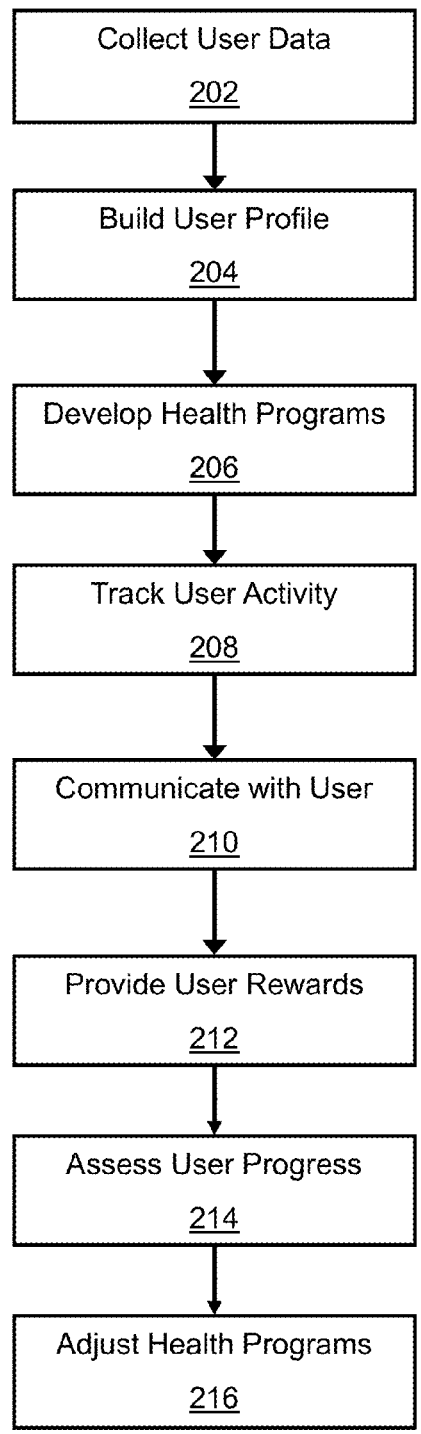
FIG. 6 illustrates a method of improving a user's health and wellness, according to one embodiment of the invention.
Figure 7:
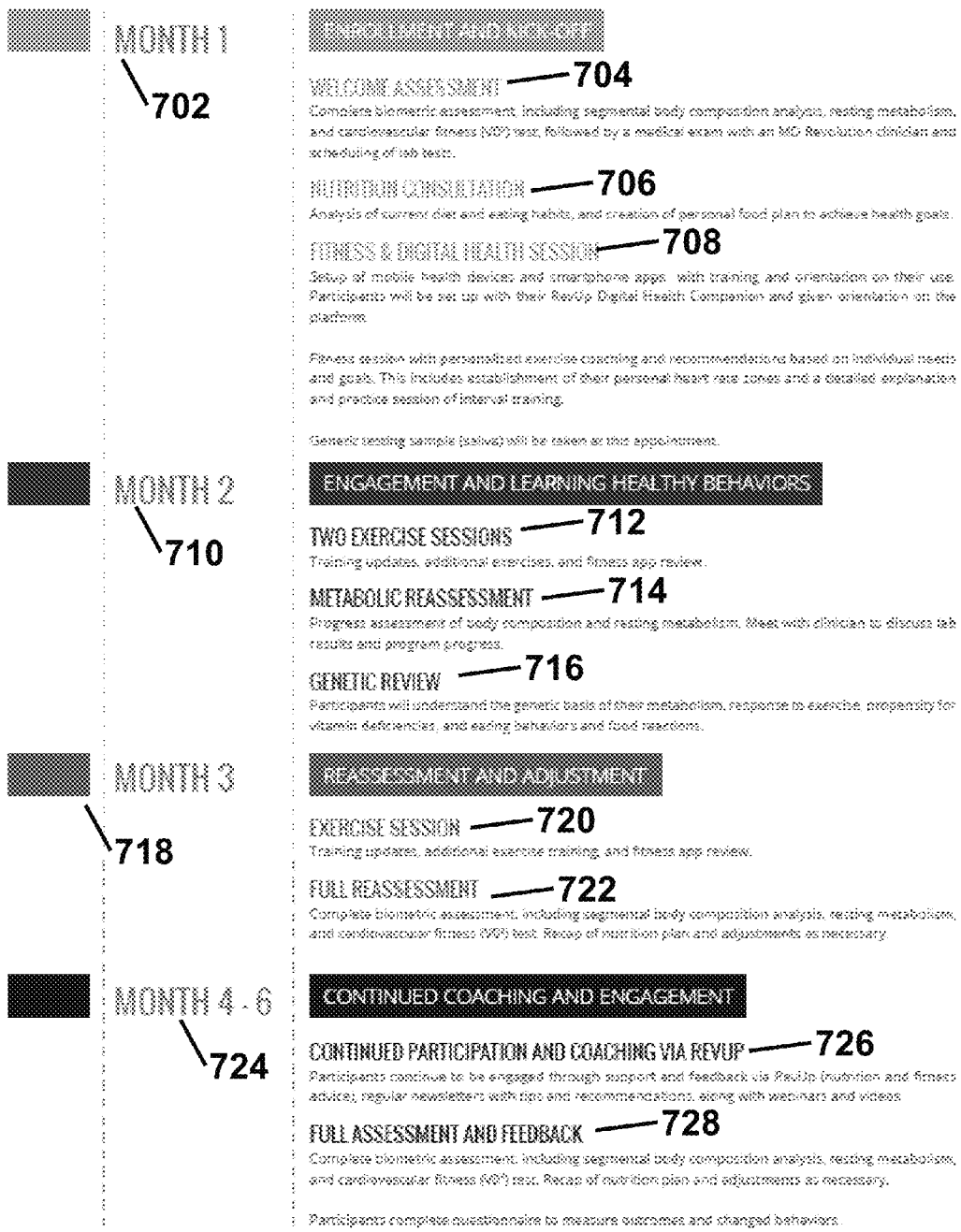
FIG. 7 is an illustration of a time-based implementation of a method of collecting and analyzing user-specific data to develop comprehensive, personalized health and wellness programs, according to one embodiment of the invention.

FIG. 6 illustrates one embodiment of a method of improving a user's health and wellness, according to one embodiment of the invention. In a first step 202, data on the user is collected, such as information on the user's medical, genetic, fitness and nutrition. Existing medical conditions, genetic predispositions, exercise abilities including body performance testing, diet, caloric intake, etc. may all be collected. In a next step 204, a user profile is developed which summarizes the health and wellness of the user based on the collected data. Grading, scores and other ratings are also determined with the user profile to provide an easy to understand metric that assesses the user's overall health and wellness and their risks for morbidities. The grades and other scores, along with specific identified risk factors, will be utilized to develop health and wellness programs in step 206. The health and wellness programs are customized to address the user's specific factors that are identified as causes of high risks of morbidity, such as visceral fat, excess body fat, low oxygen consumption, poor posture and low RMR. The program includes recommendations for specific exercise, nutrition, diet, activity, sleep and health care treatment. In step 208, once the user is provided with their program, the user is provided with one or more wireless health devices and applications to track their participation in the program. This includes tracking their general activity (steps, exertion, sleep), heart rates and recovery (such as during a workout), caloric intake and food type, weight, BMI, etc. The activity may be tracked and entered through separate devices configured for each measurement parameter or through a combined device integrated into a portable electronic device such as a smartphone or tablet. The portable electronic device may run applications which receive the data and transmit it to the dashboard server, and other wireless health devices may be configured to transmit the data through their own device servers to the dashboard server. The user is also provided with the interactive dashboard graphical user interface, where they can view and track their activity and progress and communicate with plan administrators, healthcare professionals and other users (step 210). In step 212 the user may be provided with points and rewards as an incentive for completing and progressing through various steps of the plan. In step 214, the user's progress may be evaluated at certain time points during the plan to assess their progress and physiological changes. The user's progress, whether good or bad, and the newly received information from the assessment and the wireless health devices, may be utilized to adjust the program in one or more aspects to help the user more effectively achieve their goals (step 216). For example, as the user begins an exercise program and increases their RMR and VO2 and decreases their heart rate recovery, their recommended caloric intake and food balance may be adjusted to account for their increase in calories burned, or their heart rate and heart rate recovery goals may be adjusted based on their recently collected data. These adjustments may be made in real-time as the data collected from the mobile health devices is received or as the user's health is re-assessed at regular intervals. The parameters of the health and wellness program may be individually adjusted, and the parameters may be adjusted to reduce or simplify the requirements of the program if the user's activity has dropped or the user's health is re-assessed to be lower than a previous assessment. The adjustments may then be displayed to the user on the dashboard graphical user interface or transmitted via a notification so the user can implement the changes in real-time The timeline and specific steps of the system and method are set forth in further detail in FIG. 7. In a first enrollment and kick-off step 702 scheduled for Month 1, initial assessments 704 and consultations 706 are performed on the user, including a biometric assessment, segmental body composition analysis, resting metabolism and cardiovascular fitness (VO2) test. This is followed by a medical examination with a clinician and the scheduling of lab tests. Genetic testing is also performed in this step in order to obtain data that may be relevant to the user's overall medical condition, health and fitness ability and nutritional predispositions. The enrollment step also includes a nutrition consultation 706 for an analysis of current diet and eating habits and the creation of a personal food plan designed to achieve health goals. The user will then be provided with a fitness assessment 708 personalized to their current level of fitness in order to develop specific recommendations for exercise and activity that will help them improve as quickly as possible. The fitness assessment 708 includes establishing a personalized heart rate zone and a detailed explanation of the fitness and exercise program of interval training Finally, the user will be issued one or more mobile health devices and related software (such as a smartphone app) for tracking and monitoring their activities.

In Month 2, the user begins (at step 710) engaging with the system and learning healthy behaviors as they begin following the program instructions for exercise, nutrition and any medical interventions. This may include monitored exercise sessions 712 where the user is guided through the fitness interval training to maximize their heart rates and reduce their overall recovery time. During Month 2, the user may be reevaluated (step 714) with regard to their RMR and body composition to discuss their short term progress. A detailed genetic review 716 may also be completed as this stage to help the user understand the genetic components of their metabolism, response to exercise, propensity for vitamin deficiencies, eating behaviors and food reactions.

In Month 3 (step 724), a complete reassessment of the user is completed in order to adjust the user's training and exercise, caloric intake, etc. based on their progress. A complete biometric assessment 728, including segmental body composition analysis, resting metabolism and cardiovascular fitness (VO2) test is performed again in order to compare with previous results. A review of the nutrition plan may also be completed, and adjustments made based on the user's progress, improvements and compliance.

In Month 4-6, the user is provided with continued coaching and engagement (step 726) with the system in order to keep the user involved in the program and maintaining their improved health and fitness. This includes interactions with their user profile over the dashboard and user interfaces, points systems and rewards to provide continuous incentives, and additional assessments of the user to determine if the user is maintaining or continuing to make progress toward long term goals.

The steps may be achieved over a period of time designed to provide a gradual improvement in the user's health and wellness and build good behavior without overwhelming the user with information and tasks. In one embodiment, the primary assessment, engagement and reassessments steps may be completed over a period of approximately three months, with the continued coaching and engagement steps occurring over another two months to ensure continued compliance with the program. However, the program could ideally continue indefinitely in order to motivate the user to continue with the program and attain an ideal health profile.

III. Collecting User Data

In one embodiment, the data sources which collect and transmit data on the user may include a scale for measuring weight and body composition, a pedometer or other exercise monitor which measures steps and calories burned, a heart rate monitor, a continuous glucose monitor, a blood pressure monitor and a sleep monitor. These devices are only exemplary, and numerous other health, fitness, environment and nutrition monitoring devices may be implemented and used to generate user data. These devices may be added to a user's account so that the device can transmit data to the front-end cloud server, either wired or wirelessly through a connection to a network or with a user's computer or portable electronic device running software which receives data from the third party data sources and transmits it to the front-end cloud server. Many wireless health devices have open application programming interfaces (APIs) which allow them to be easily integrated with a system running on the front-end cloud server that will compile, analyze and display the data.

The type of data that may be collected about a user relates to the user's medical, genetic, fitness, environment and nutrition. The medical data may include general information on disease or known health problems, but may also include specific physiological or biochemical measurements, examples of which include heart rate, resting metabolic rate (RMR), $VO_2$, weight, body fat, visceral fat, muscle mass, body water, body mass index (BMI), bone mass and blood glucose. Genetic data may include core genomic information and more targeted genomic information that specifically relates to known genetic correlations with disease, nutrition, fitness and behavior. Fitness data may relate to exercise routines, types of workouts, length of time spent on exercise, calories burned, heart rates achieved, etc., while environmental data may relate generally to a user's lifestyle choices, such as sleep, smoking habits, commute times to works and hobbies and sports. Nutrition data may include information on the types of foods eaten, the calories consumed, the number of meals and snacks, beverages and alcoholic consumption, etc.

As illustrated in FIG. 8A and FIG. 8B, assessing the user's VO2 and heart rate recovery time is another data point to be collected in order to assess the user's overall health and fitness. The chart in FIG. 8A shows a list of time intervals 802 in a first column with a corresponding workload (speed/incline) value 804 in the second column of an exercise machine such as a treadmill. As time progresses, the speed/incline increases, which has a corresponding effect on the user's VO2, as provided in the third column 806. During the assessment, the healthcare professional or evaluator will enter the user's heart rate in beats per minute (BPM) 808 at each time interval in order to gauge the user's overall fitness and ability in terms of a maximum heart rate. A recovery period 810 is also measured at the end of the workload application, for example for about two minutes—in order to determine the ability of the user's heart to recover from the applied work. The recovery period is another key factor in assessing the user's overall health and fitness, and this recovery period metric will be used throughout the system to determine if the user's cardiac health and fitness is improving.

FIG. 8B shows a similar chart, but with increased speed/incline values 804 and corresponding increased VO2 values 806. Multiple graduated increases in workload may be provided during a user assessment at various stages of the embodied methods in order to gradually increase the workload on the user and increase their overall VO2 and RMR levels. As is evident from a comparison of the VO2 levels 806 in FIG. 8A and the VO2 levels 806 in FIG. 8B, the goal is to gradually increase the user's fitness to the point that their measured heart rates 808 are the same even though the workload and VO2 has significantly increased.

IV. Aggregating and Analyzing Data

In one embodiment, data from employees, patients and consumers are acquired via health assessment questionnaires, six independent wirelessly enabled mobile health-tracking devices that measure resting metabolism, blood pressure, blood glucose, heart rate during exercise, steps per day, activity/movement levels via an accelerometer, weight and body composition via a scale, cardiorespiratory fitness levels as defined by $VO_2$ (oxygen consumption during submaximal exercise testing) and calorie consumption. Additional laboratory data and genetic information are aggregated and analyzed as described below.

Age, weight, body mass index, gender, HDL cholesterol, LDL cholesterol, triglyceride levels, adiponectin, lipoprotein (a) levels, and systemic inflammation as defined by high sensitivity CRP are collected and key co-morbidities including obesity, diabetes, diabetes control, hypertension, coronary artery disease, prostate cancer, breast cancer, colon cancer, lung cancer, smoking status are all ascertained at the beginning of the assessment process.

Key genetic information is strategically acquired and includes polymorphisms indicating susceptibility to breast cancer, lung cancer, colon cancer, prostate cancer, hypertension, stroke, atrial fibrillation, coronary artery disease, diabetes, and obesity. Key genetic susceptibilities to vitamin deficiencies, blood pressure and diabetes response to exercise, and key behaviors related to psychosocial factors including eating disinhibition and satiety are recorded in the existing database.

Once all of the user data has been collected, the data is analyzed in order to generate a user profile which not only summarizes the data collected about the user but also provides analytical results about the user's health and wellness. As previously described above, FIG. 4 illustrates the interrelationships between the data collected by several data sources and the use of this data in generating the components of the user profile. The data sources may include mobile health devices, metabolic health assessments, genetic and traditional laboratory testing and personalized nutrition and fitness plans, although this list is not limiting by any means. Data on the user's health and wellness is collected from all of these data sources and then considered separately or in conjunction with one another in order to provide personalized health and wellness programs with recommendations on an interactive dashboard graphical user interface. The data is optimized to the benefit of the user by factoring in data from all of these data sources when generating recommendations for the user to improve his or her health and wellness Ranking and rating systems are developed based on knowledge of which factors and comorbidities and which levels of those factors lead to improved health and wellness, reduced mortality, and better quality of life.

In one embodiment, the system ranks the health of a patient based on six key performance metrics tied to reduced chronic disease and death. The grading system is applied after cross referencing the database of comorbidities, genetic testing, and standard laboratory testing noted above The six key performance metrics include visceral fat, body fat in percentage, resting metabolism as defined by calories of intake per day and overall oxygen consumption at rest (ml/kg/min), cardiorespiratory fitness, biomechanical assessment (that includes a posture screen), and overall bone density.

A segmental body scan is done to determine the individual's body fat percentage expressed as a total body fat percentage and then broken down to each arm, each leg, and trunk. It also gives segmental body fat in pounds for each leg, arm, and trunk/visceral fat. Being able to determine the pounds of visceral fat is very unique and is used as an important health risk appraisal. The scan also tells body water, muscle mass and bone mass.

Resting metabolism is established based on the individual's ability to process oxygen at rest (VO2). It also gives the exact caloric intake the user should have to reach their weight goal, be it to lose weight, maintain weight, or gain weight. Resting metabolism varies widely across populations.

A method to assess baseline and follow up cardiorespiratory fitness scores are performed and are based on the individual's ability to process oxygen while exercising.

A bio-mechanical screen can quickly determine any posture/core imbalances that an individual has that might lead to injury and or back and joint pain. The assessments consist of 5 kinetic check points: head, shoulder, hips, knees, and feet.

Resting metabolism, body composition analysis, and cardiorespiratory fitness provide critical user profile data that is leveraged to establish a personalized health, fitness, and nutrition plan. Re-assessments are done at four week intervals to track progress with nuanced changes being incorporate and conveyed to the user either in person or the graphical user interface of the software application.

Health Grading System

One embodiment of a grading system as applied to an individual who is 55 years of age and with one chronic disease risk factor would look like the following. Resting Metabolic Rate, (VO2), Goals and Grades. Resting rate of 3.5 ml/kg/min, grade, B−. Resting rate below a 3.5 ml/kg/min, grade, C. Resting rate above 3.5-3.8 ml/k/min, grade, B. Resting rate above 3.8-4.4 ml/kg/min, grade B+. Resting rate 4.5 ml/kg/min and above an A. The above grading may change according to age, gender, and co-morbidities, and is automatically applied via an integrated software application.

When the goals are set there are several factors used to determine the goals in body comp, Resting VO2 and Exercising VO2. Age, gender and genetics can have impact on all these parameters. Not all individuals will be able to reach an A grade in each category. It is the goal to ensure that the individuals have no C's as a grade once they have completed the program.

Metabolism/VO2 decreases as we age unless we take actions to counter it. The generic values of 3.5 ml/kg/min for resting metabolism and 35/ml/kg/min are considered typical of a young healthy male. Higher VO2 at rest and when exercising is linked to greater health and longevity, therefore we set the values above the "norms" for most individuals. This allows for a decrease with age but still does not allow the person to dip below the generic population values, providing a safety net of sorts.

In one embodiment, a goal is set of VO2 exercising to be 12 times that of their resting V02 for most individuals. That would result in a grade of B. If the individual has a VO2 between 10 and 12 times their resting they receive B−. If the VO2 is between 12-14 times their resting they receive a B+. A VO2 greater than 14 times their resting is an A. If the individual has VO2 less than 10 times their resting they receive a C. The above grading changes according to age, gender, and co-morbidities and is automatically applied via the integrated software application.

Body Fat Percentage is based on the individual's baseline athletic ability or history of athleticism. Being able to obtain very low body fat % levels is based greatly on genetics of the individual. If they do not fall into the "Athlete" definition a less aggressive goal is set. Age, gender and genetics are all factors in determining body fat % goal.

The main focus on body composition is to decrease visceral/trunk fat as higher levels of visceral/trunk fat are tied to inflammation, heart disease and cancer. The athletic individual would have a goal of visceral fat of 10 lb. or less. For the majority the goal is between 15 or 20 lb. depending on existing co-morbidities. Those with 1 risk factor have a goal visceral fat level of less than 15 pounds. The scientific community states a visceral fat of 50 lb. or more (Visceral Score of 10 or higher) is a significantly high risk for major health issues. A visceral fat of 20 or less pounds is realistic if their exercise and nutrition is appropriate. This keeps the individual well below the significant health risk level. A visceral fat level of 10 lb. or less would be a score of A− or A. A visceral fat level of 11 lb-20 lb would be a score of B+ or B. A visceral fat score above 21 lb-25 lb. would be a B−. Anything 26 lb. above would be C.

Bone Mass Grade is based off a scale that has been determined by scientific community as average or below average and it is determined by the weight in bone the person has in comparison to the persons overall weight. If the person has average bone mass as predetermined by a scale the person gets a B, if the individual has below average bone mass they receive a C, if the person is well above the average value the receive an A.

Posture/Core Screen—As stated above posture and lack of core strength can lead to muscle, joint and back pain which also leads to decreased activity, productivity and often pharmaceutical use in individuals. Individuals who are older, 68 or above, who have these issues have limited range of motion and lack of balance. They are more likely to fall and break a bone. If all 5 kinetic chain check points are satisfactory the individual receives a grade of an A. If the individual has one kinetic check point that is not satisfactory the individual receives a B−. If the individual has more than one kinetic check point that is not satisfactory then the individual receives a C.

RevUp Age Calculation

Another grading mechanism is the calculation of the user's "RevUP age," which is a measurement of the user's actual age based on their VO2 max (mL/kg/min) measurements or heart rate recovery. An individual's VO2 is highly correlated with age, so this RevUp age score provides a numerical value that is easy for a user to understand and which clearly indicates the effect (positive or negative) on their age as a result of their VO2. The user's RevUP age is a metric of their overall health in years as compared with their actual chronological age, where their RevUp age may be less than their actual age if they have a good VO2 level, but more than their actual age if they have a poor VO2 level, as indicated by the exemplary guidelines in Table 1 and Table 2, below:

TABLE 1

| GENDER | AGE | POOR | FAIR | AVERAGE | GOOD | EXCELLENT |
|---|---|---|---|---|---|---|
| MEN | ≤29 | ≤37.9 | 38-41.6 | 41.7-45.5 | 45.6-50.9 | ≥51 |
|  | 30-39 | ≤36.6 | 36.7-40.6 | 40.7-43.9 | 44-47.9 | ≥48 |
|  | 40-49 | ≤34.7 | 34.8-38.3 | 38.4-42.3 | 42.4-45.9 | ≥46 |
|  | 50-59 | ≤31.9 | 32-35.4 | 35.5-38.9 | 39-42.9 | ≥43 |
|  | 60-69 | ≤28.6 | 28.7-32.2 | 32.3-35.5 | 35.6-38.9 | ≥39 |
|  | 70-79 | ≤25.6 | 25.7-29.3 | 29.4-32.3 | 32.4-35.9 | ≥36 |
| WOMEN | ≤29 | ≤32.1 | 32.3-36.0 | 36.1-39.4 | 39.5-42.9 | ≥43 |
|  | 30-39 | ≤30.8 | 30.9-34.1 | 34.2-37.6 | 37.7-42.9 | ≥42 |
|  | 40-49 | ≤29.3 | 29.4-32.7 | 32.8-35.9 | 35.9-38.9 | ≥39 |
|  | 50-59 | ≤26.7 | 26.8-29.8 | 29.9-32.5 | 32.6-35.9 | ≥36 |

TABLE 1-continued

| GENDER | AGE | POOR | FAIR | AVERAGE | GOOD | EXCELLENT |
|--------|-----|------|------|---------|------|-----------|
| | 60-69 | ≤24.5 | 24.6-27.4 | 27.3-29.6 | 29.7-31.9 | ≥32 |
| | 70-79 | ≤23.4 | 23.5-25.8 | 25.9-28.0 | 28.1-29.9 | ≥30 |

TABLE 2

| AGE (years) | POOR | FAIR | AVERAGE | GOOD | EXCELLENT |
|-------------|------|------|---------|------|-----------|
| ≤29 | +5 | +3 | Actual Age | −3 | −5 |
| 30-39 | +10 | +5 | Actual Age | −5 | −10 |
| 40-49 | +5 | Actual age | −3 | −5 | −10 |
| 50-59 | +5 | −3 | −5 | −10 | −20 |
| 60-69 | +3 | −5 | −10 | −20 | −30 |
| 70+ | +3 | −5 | −15 | −20 | −30 |

Chronological age: ≤29 years
If Excellent; chronological age−5=RevUp Age
If Good; chronological age−3=RevUp Age
If Average; chronological age−0=RevUp Age
If Fair; chronological age+3=RevUp Age
If Poor; chronological age+5=RevUp Age
Chronological age: 30-39 years
If Excellent; chronological age−10=RevUp Age
If Good; chronological age−5=RevUp Age
If Average; chronological age−0=RevUp Age
If Fair; chronological age+5=RevUp Age
If Poor; chronological age+10=RevUp Age
Chronological age: 40-49 years
If Excellent; chronological age−10=RevUp Age
If Good; chronological age−5=RevUp Age
If Average; chronological age−3=RevUp Age
If Fair; chronological age−0=RevUp Age
If Poor; chronological age+5=RevUp Age
Chronological age: 50-59 years
If Excellent; chronological age−20=RevUp Age
If Good; chronological age−10=RevUp Age
If Average; chronological age−5=RevUp Age
If Fair; chronological age−3=RevUp Age
If Poor; chronological age+5=RevUp Age
Chronological age: 60-69 years
If Excellent; chronological age−30=RevUp Age
If Good; chronological age−20=RevUp Age
If Average; chronological age−10=RevUp Age
If Fair; chronological age−5=RevUp Age
If Poor; chronological age+3=RevUp Age
Chronological age: 70+ years
If Excellent; chronological age−30=RevUp Age
If Good; chronological age−20=RevUp Age
If Average; chronological age−15=RevUp Age
If Fair; chronological age−5=RevUp Age
If Poor; chronological age+3=RevUp Age As indicated above, the measured VO2 level is matched in Table 1 with a customized range that is identified with a rating classified as Poor, Fair, Average, Good or Excellent. Next, their chronological age is used to determine the number to add or subtract from their chronological age based on their rated VO2, as indicated in Table 2. For example, a 60 year old male patient has a VO2max of 53. Using the <29 yrs as a baseline, this individual would fall in the excellent category and receive a 20 year reduction in his chronological age. His RevUp age would be 30 years. In another embodiment, the RevUp age may be calculated as a factor of the user's heart rate recovery, which is also another indicator that highly correlates with the user's overall health.

Creating a User Profile

After all grading systems are applied and goals set according to general parameters listed above and key genetic determinants such as susceptibility to key chronic diseases enable more stringent grading and setting of higher goals. Such information has proven highly motivational. Genetic variants for key vitamin deficiencies enable a personalized nutrition plan. Genetic data on blood pressure response to exercise and effects with respect to endurance and strength training enable personalized fitness regimens. Heart rate zones are set based on these data and overall fitness levels noted above. Patients then follow this personalized regimen and are tracked via the continuous monitoring provided by the wireless devices noted above. Constant feedback is provided via a graphical user interface of the integrated software application.

The user data is analyzed in order to generate a user profile which summarizes a multitude of health and wellness information about the user and provides metrics for assessing the user's health and wellness. The user profile may provide an overall summary or numerical value ranking of the user's health in addition to specific rankings and evaluations of specific physiological or biochemical measurements.

Figure 9:
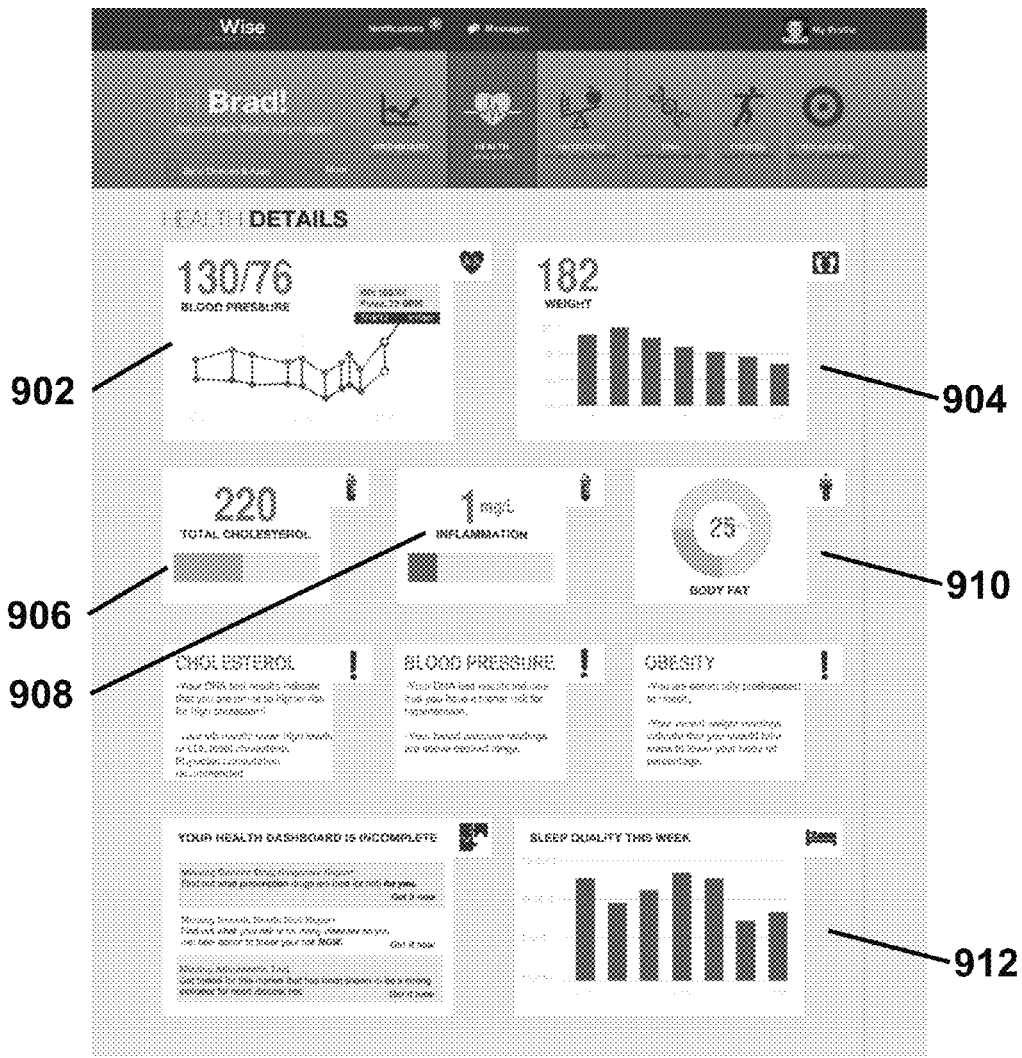
FIG. 9 is an illustration of a graphical user interface (GUI) health and wellness dashboard which displays user profile and health and wellness program data to the user, according to one embodiment of the invention.

FIG. 9 illustrates one embodiment of a dashboard graphical user interface (GUI) 900 which lists a plurality of physiological data, including blood pressure 902, weight 904, total cholesterol 906, inflammation 908, body fat percentage 910, and sleep quality 912. Some of this information is displayed in graphical form to show historical data over a period of time, helping the user determine if they are moving in a certain direction. For example, the user in FIG. 9 is making progress in losing weight as evidenced by the chart 904, while the blood pressure chart 902 indicates that blood pressure is increasing. Some information may be displayed using color-coded graphical information, such as a yellow-colored bar for the total cholesterol level of 220 that is considered potentially unhealthy. In contrast, the indicator for inflammation is a green bar, as the measured level (1 mg/L) is within healthy levels.

Figure 10:
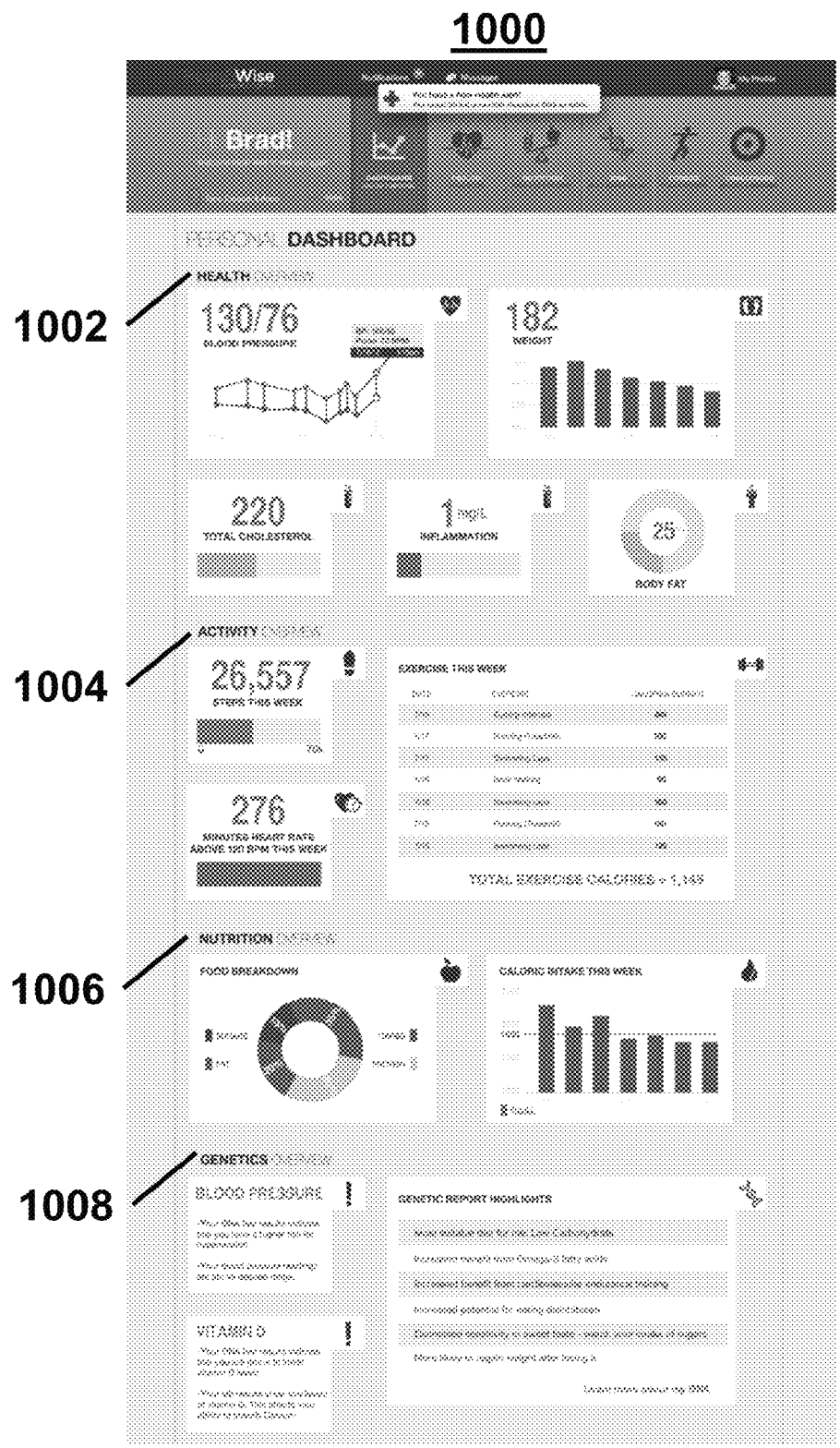
FIG. 10 is an illustration of a further embodiment of the health and wellness dashboard displaying a plurality of user-profile data and health and wellness program data to the user, according to one embodiment of the invention.

FIG. 10 is an illustration of a GUI of an overall health and wellness dashboard 1000 which provides a summary of information from several different categories, including physiological data 1002, fitness data 1004, nutrition data 1006 and genetic information 1008. Specifically, FIG. 9 provides a chart with a Nutrition Overview 1006 indicating a breakdown of the levels of fat, sugar, carbohydrates and protein in the food consumed by the user over a period of time. A genetic report table 1008 may also list one or more suggestions for the user based on information obtained from the user's genetic profile, including nutrition advice, fitness advice and warnings about susceptibility to weight gain or certain diseases such as diabetes.

In one embodiment, the user profile includes general health statistics, such as age, height and weight, along with specific measurement values, such as a resting metabolic rate (RMR) at ml/kg/min at kcal/day, fitness levels (VO2 at ml/kg/min), caloric intake, body composition, visceral fat, and even physical body profile information such as alignment of joints, muscles and movement capabilities.

Figure 11:
FIG. 11 is an illustration of a computing device displaying the dashboard GUI, according to one embodiment of the invention.

In one embodiment, the user profile may be displayed as a graphical user interface (GUI) 1102 to the user on a client dashboard interface such as a computer 1104 with a display or a tablet, smartphone or other portable electronic device, as shown in FIG. 11. The client dashboard interface preferably has one or more input devices such as a mouse, keyboard or touchscreen with which the user can interact with the GUI. The GUI may be organized as a "dashboard" that provides the user with helpful summaries of a plurality of different information relating to their genetics, health, fitness, environment and nutrition in the form of visual aids on the dashboard. The information may be presented with an easily-understandable chart, graph or relevant numerical value that will help the user quickly glance at the dashboard and determine an overall sense of their current level of health and wellness, their progress toward established health and wellness goals and other pertinent information. Genomic and nutrigenomic data gathered from genomic profiles of the user may also be incorporated, such as a recommended diet type, predisposition for high blood pressure or high cholesterol, recommendations for types of exercise, and nutritional optimization (for example, if the body responds well to certain vitamins and nutritional components). In addition, health predictor tests that indicate predispositions to diabetes, cancer, etc may also be used and incorporated into the dashboard and recommendations provided therein. A drug response test that tests a user's response (or lack thereof) to prescription drugs may also be incorporated.

Further details with regard to the dashboard GUI and its related features and functions will be provided in Section VI and the related figures, below.

V. Developing Health and Wellness Programs

In one embodiment, customized health and wellness recommendations are developed based on medical and health-related information on the interrelationships of this data. The ratings and rankings of user data determined from the above analysis will inform one or more target factors of the user's health which may fall below standard or recommended levels. Additionally, data on the user's genetic information may provide information which leads to a specific recommendation. For example, a user may be identified to have a particular genetic trait related to satiety which is known to cause a person to need to feel like they have a full stomach. If this trait is identified in the user, the health and wellness program will recommend that the user eat certain foods at certain times during the day in order to continually feel full without eating high caloric or high fat foods.

Fitness-Based Interventions

In one embodiment, the health and wellness programs may provide recommendations for fitness-based interventions such as cardio exercise which will increase the user's RMR, exercises which will achieve a certain heart rate, and diets which will reduce certain levels of fat or cholesterol that were identified as problematic in the user profile. A customized cardio interval exercise program may be used which provides for achieving varying levels of heart rate at varying time intervals over a period of time. The interval training program is designed to maximize the increase in RMR and the loss of visceral fat. The user is asked to perform a cardio-based exercise (walking or running) over specified time intervals while monitoring their heart rate in order to achieve certain heart rates at certain time intervals.

Interval training can yield numerous health benefits such as improvements in VO2max and decreasing body fat percentage including visceral fat. VO2max is an important indicator of cardiorespiratory fitness. Interval training consists of vigorous intensity periods of exercise. Greater improvements in VO2max have resulted from vigorous intensity exercise than moderate intensity exercise. Several studies have examined various volumes of interval training for health benefits. It has been shown that shorter duration, higher intensity interval programs have been effective in improving VO2max and decreasing body fat including visceral fat weight.

In one embodiment, several target heart rates to achieve at various times during the exercise are developed based on a Maximum Heart Rate (in BPM, or beats per minute) calculated for each user based on their fitness assessment. In one embodiment, the target heart rates are set as follows:

Max Effort=Max Heart Rate−15 BPM
Hard Work=(Max Heart Rate−20)−10
Warm up/Recovery=(Max Heart Rate−40)−10

For example, with a Max Heart Rate=200, the target heart rates during exercise would be:

Max Effort=200-185
Hard Work=180-170
Warm up/Recovery 160-150

Next, the user is asked to exercise for a certain interval of time at each target heart rate and then repeat the interval as needed in order to achieve a varying level of heart rate during the exercise. One example of a Performance Improvement Interval, designed to increase the user's overall physical ability and RMR would be:

10 minute Warm-up
60-90 seconds Difficult
1 minute Max Effort
60-90 seconds Recovery
Repeat 4-6 intervals In another embodiment, a Medical Interval may be developed for a user with an underlying medical or health issue that prevents them from achieving normal goals for exercise and health. The Medical Interval may be:

10 minute Warm-up
2 minute Difficult
1 minute Max Effort
90-120 seconds Recovery
Repeat 7 intervals The intervals may be developed based on each user's own perceived levels of exertion, which can then be dynamically adjusted as the user completes their exercise goals. For example, one set of Intervals and Perceived Exertions would be:

Warm-up/Recovery Interval: Perceived Exertion Rate 6 (Comfortable work)
Difficult Interval Perceived Exertion Rate 7-9 (Hard to very hard)
Max Effort Interval: Perceived Exertion Rate 10 (Maximum effort)

However, as the user continues to exercise using the cardio-based interval program, their perceived levels of exertion will decrease for each interval and corresponding heart rate. The exercise program may therefore dynamically adjust the intervals and corresponding Max Heart Rate as the user completes several exercise sessions. Over time, as their Max Heart Rate increases, their RMR will also increase, and in the process, their levels of visceral fat and other unhealthy factors will also begin to decrease.

Nutrition-Based Interventions

Each user will be provided with a nutritional assessment based on their genetic, health and fitness evaluation which is designed to help the user consume foods which will maximize their health, decrease risk factors and target any genetic predispositions for certain types of foods that may particularly benefit the user. In addition, the user will be provided with a calorie goal for daily calorie consumption that includes the types of calories to consume (protein, carbohydrates, fat) and how many calories to consume at certain times of day (breakfast, lunch, dinner, morning snack, afternoon snack, pre- and post-workout snack, etc.). All of these nutritional recommendations are developed to reduce visceral body fat and are additionally customized for each user. The user will then be directed to track their food consumption in terms of the number of calories and types of calories, which will then be evaluated to ensure that the user is keeping up with their caloric and nutritional goals.

Automation of nutrition feedback will rely on the combination of a thorough health risk questionnaire, lab data, biometric data, anthropomorphic data, resting metabolic rate, genetic data, food allergies and intolerances, dietary restrictions, and food preferences.

Examples of nutritional goals and information include:
Daily caloric breakdown:
 a. Based on daily activity level
  i. Non-exercise
  ii. Medium intensity
  iii. High intensity
Daily macronutrient balance:
 a. Carbohydrate: 40-50%
 b. Protein: 30-40%
 c. Fat: 20-30%
Macronutrient recommendations:
 a. Complex carbohydrates
  iv. Fruit, vegetables, whole grains
 b. Lean Protein
  v. Poultry, fish
 c. Healthy fats
Portion control:
 a. Serving sizes
Daily food routine:
 a. Eating every 4-5 hours
  vi. Blood sugar stability and boost metabolism
Food logging:
 a. Promoting healthy behavior change
Supplementation.
 a. If deficiencies indicated If the user logs their food 1-2 times per week they receive an email intended to reinforce the positive behavior of food logging. The content of the email is detailed and specific to the patient, and includes tips, suggestions, and recommendations designed to keep the patient engaged in food logging.

As shown in FIG. 9, the recommendations may indicate a genetic risk for high cholesterol and as a result indicate that further consultation with a doctor or dietician is needed in order to determine what foods will minimize the user's predisposed risk.

Medical and Genetic-Based Interventions

The recommendations may also be medical in nature, such as recommending that the user begin taking one or more medications to treat disease (such as diabetes) or reduce risks of determined genetic conditions such as high cholesterol. If a serious genetic condition is identified, the user may be provided with options for genetic therapy The user interface in FIG. 9 and FIG. 10 may include a recommendations section which displays one or more recommendations to the user in order to help achieve one or more goals with regard to the user's health and wellness. The recommendations may be based on the user's profile and be updated based on current information that is periodically or constantly being input to the front-end cloud server by the third party data sources.

VI. The Dashboard: Monitoring and Tracking User Progress

Once the user is presented with one or more health and wellness programs and their user profile, the user may begin to implement the recommendations by making changes related to their fitness, nutrition and environment. The user may also make medical changes, such as taking a drug to reduce cholesterol or having a surgical procedure to reduce an identified risk factor. The mobile health devices may provide the means to track the user's progress toward identified goals in their health and wellness programs, by measuring the same categories of data that were initially measured when developing the user profile. In this way, the mobile health devices are integral to monitoring a user's progress and evaluating the success of the health and wellness programs. Modifications may be made on a regular basis to the health and wellness programs based on the constant stream of data that may be received from the mobile health devices and applications that the user interacts with in order to track their health.

The user profile may be displayed via an interactive dashboard graphical user interface (GUI) to users, administrators and healthcare professionals so that each interested party can not only view the data but also interact with the dashboard to provide additional recommendations to the user for improving certain aspects of their health and wellness based on the data shown in the dashboard. Changes made to the dashboard by these parties may be sent back to the front-end cloud server to immediately revise the dashboard content, and the changes may also be stored in the dashboard database for future display. The dashboard may therefore be continually revised based on the health and wellness data collected on the user and the information input by the interested parties that view the dashboard.

FIG. 3 illustrates one embodiment of a system and method of generating the interactive health and wellness dashboard, according to one embodiment of the invention. In this embodiment, data on a user is collected from a plurality of sources, such as a mobile health device, a mobile application on a portable electronic device or through manual user entry via a computing device. The mobile health devices and mobile applications may be configured to collect information on the user as the user wears or uses the device. In one embodiment, these devices may communicate with one or more device or application servers that receive data collected and then communicate with a dashboard database of a front-end cloud server to collect the data for generating the dashboard. In addition to the devices, additional user data may be collected at the dashboard database in the form of genomic data from a genomic report or lab results from lab tests that the user has undergone. The dashboard database will collect all of the medical, genetic, fitness, environmental and nutrition information about the user that will then be used to generate the dashboard. These devices may be configured to continually collect and report data to the dashboard database in real-time or at periodic increments so the dashboard can be continually updated to provide the most relevant information about the user's health and wellness. Some devices may require user input, such as a nutrition application running on a portable electronic device in which the user inputs dietary and nutrition information, and the user may be responsible for submitting the data manually as it is entered or at periodic time periods after a certain amount of data is collected. In some embodiments, the nutrition data may be obtained from mobile health devices or at least more accurately tracked by software or applications running on the portable electronic device (such as a tablet or smartphone). Similarly, some user fitness data may be generated or reported by a user.

Once the user data is collected at the dashboard database, the front-end cloud server will request the data in order to generate the health and wellness dashboard. In this embodiment, the data in the dashboard database is protected by a secure firewall, and additional firewalls may be placed throughout the system to protect data being transmitted across the system. The front-end cloud server then analyzes the data using proprietary algorithms to compare data, analyze it for patterns and then generate the health and wellness dashboard with user-specific health and wellness information based on all of the available data. The health and wellness dashboard may reflect a user profile that is generated at the front-end cloud server based on analytics which may contain recommended physiological levels for weight, heart rate, etc., recommended fitness and nutrition routines, and other recommendations based on the data collected about the user.

Once the dashboard is generated, it may be transmitted to one or more destinations for display to an interested party, including the user (patient), a healthcare team responsible for the user's health, or a corporate wellness administrator set up to monitor the user's progress toward specific health goals. The dashboard may be interactively displayed to each of these destinations so that each interested party can not only view the data but also interact with the dashboard to provide additional recommendations to the user for improving certain aspects of their health and wellness based on the data shown in the dashboard. Changes made to the dashboard by these parties may be sent back to the front-end cloud server to immediately revise the dashboard content, and the changes may also be stored in the dashboard database for future display. The dashboard may therefore be continually revised based on the health and wellness data collected on the user and the information input by the interested parties that view the dashboard.

Dashboard Organization and Interaction

Figure 12:
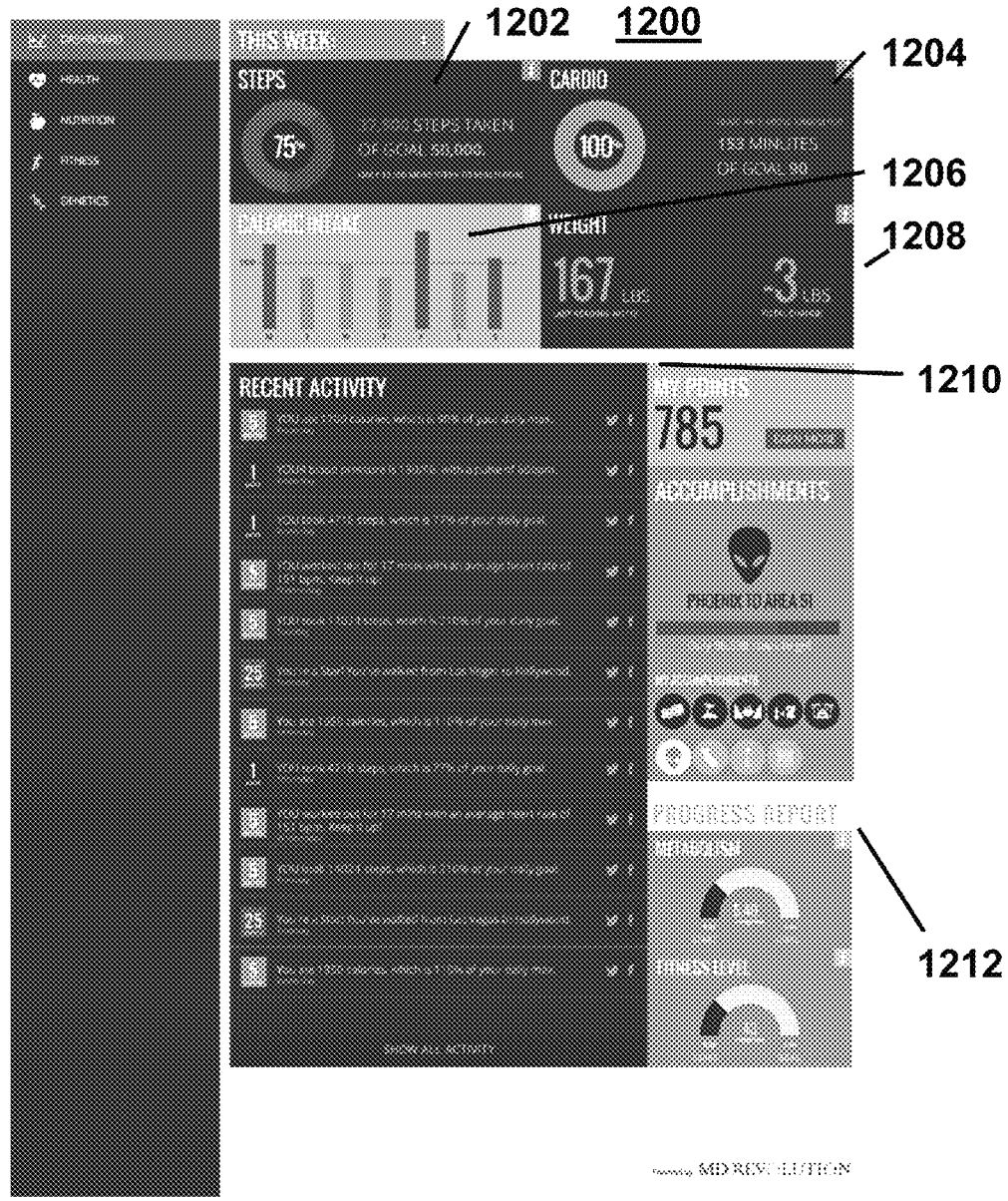
FIG. 12 is a further illustration of a dashboard GUI, according to one embodiment of the invention.

Once the data is correlated and analyzed, a graphical user interface (GUI) may be generated and displayed to the user on a client dashboard interface such as a computer with a display or a tablet, smartphone or other portable electronic device, as illustrated in FIG. 12. The client dashboard interface preferably has one or more input devices such as a mouse, keyboard or touchscreen with which the user can interact with the GUI. The GUI may be organized as illustrated in FIG. 9, as a "dashboard" that provides the user with helpful summaries of a plurality of different information relating to their genetics, health, fitness, environment and nutrition in the form of visual aids on the dashboard. The information may be presented with an easily-understandable chart, graph or relevant numerical value that will help the user quickly glance at the dashboard and determine an overall sense of their current level of health and wellness, their progress toward established health and wellness goals and other pertinent information. Genomic and nutrigenomic data gathered from genomic profiles of the user may also be incorporated, such as a recommended diet type, predisposition for high blood pressure or high cholesterol, recommendations for types of exercise, and nutritional optimization (for example, if the body responds well to certain vitamins and nutritional components). In addition, health predictor tests that indicate predispositions to diabetes, cancer, etc may also be used and incorporated into the dashboard and recommendations provided therein. A drug response test that tests a user's response (or lack thereof) to prescription drugs may also be incorporated.

One embodiment of the dashboard 1200 is illustrated in FIG. 12, which displays graphics indicating the user's steps 1202, cardio goal 1204, caloric intake 1206, weight 1208 as well as additional information on this data, such as a history of caloric intake 1202 for a preceding week, a change in weight 1208 over a period of time, or a graphic indicating the percentage of steps 1202 achieved toward a goal. An activity section 1210 displays all recent activity relating to the program, such as accomplishments, data entered, points and rewards, goals, alerts, requirements, suggestions, etc. Additional graphics on the lower right will provide an overall progress graphic 1212 toward an overall program goal, such as increased RMR, fitness, metabolism, weight, etc. The user may be able to select any one of these graphics to see a more detailed breakdown of a specific data point, such as weight, for example.

Figure 13:
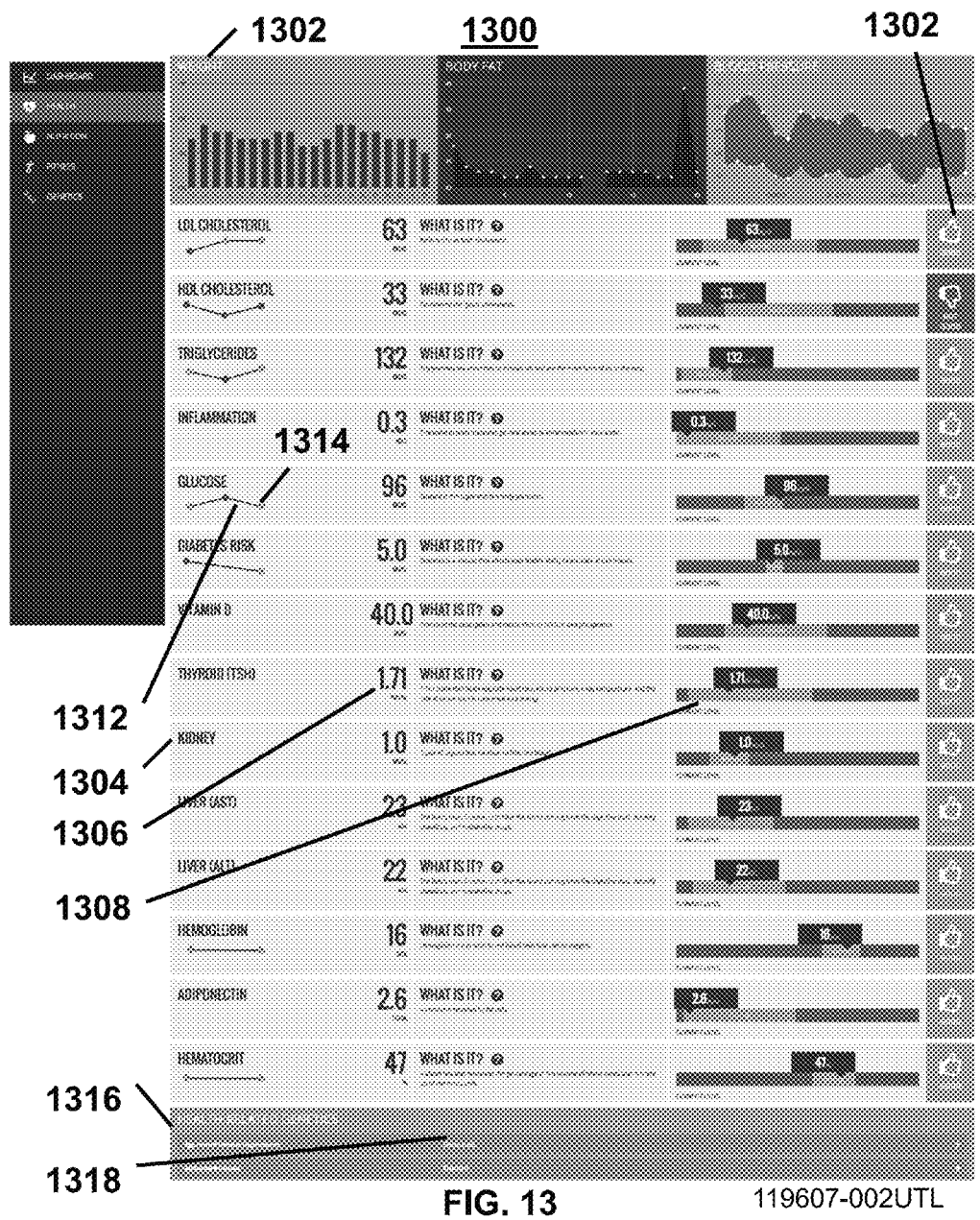
FIG. 13 is a further illustration of a health dashboard interface, according to one embodiment of the invention.

FIG. 13 illustrates a health page 1300 of the dashboard interface which provides detailed graphics and indicators for numerous health metrics which are measured and tracked by the system. The health page dashboard provides the user with a unique perspective on their overall health, as measured by at least fourteen different biometric measurements 1304, such as LDL cholesterol, HDL cholesterol, triglycerides, inflammation, glucose, diabetes risk, vitamin D, thyroid (TSH), kidney, liver (AST and ALT), hemoglobin, adiponectin and hematocrit. Graphs 1302 may show historical and current data on metrics such as weight, body fat and blood pressure so the user can see trends for these indicators individually as well as together with other metrics for comparison with each other. In one embodiment, the metrics displayed may be changed by selecting different metrics from a list below the graphs. In addition to the graphs, numerous additional metrics may be listed on the health page along with the numerical value 1306 for each metric, a slider bar graphic 1308 indicating where the numerical value falls within a range of normal or expected values for the metric, and a status icon 1310 indicating whether the numerical value is good or bad (in this illustration, a "thumbs up" indicates the value is good while the thumbs down indicates the value is bad). Additionally, a bar graph 1312 underneath the title for each metric will show historical data of that metric over previous measurements, with each circle 1314 pertaining to a measurement and the color of the circle reflecting whether the measurement was a good value (i.e. blue circle) or bad value (i.e. red circle). An additional list of health-related genetics 1316 may also be provided on the health page along with an indicator 1318 as to whether the user has an elevated, decreased, normal or other level of risk for a particular genetic trait, be it a propensity for disease or simply a behavioral component related to the user's health, nutrition or fitness.

Figure 14:
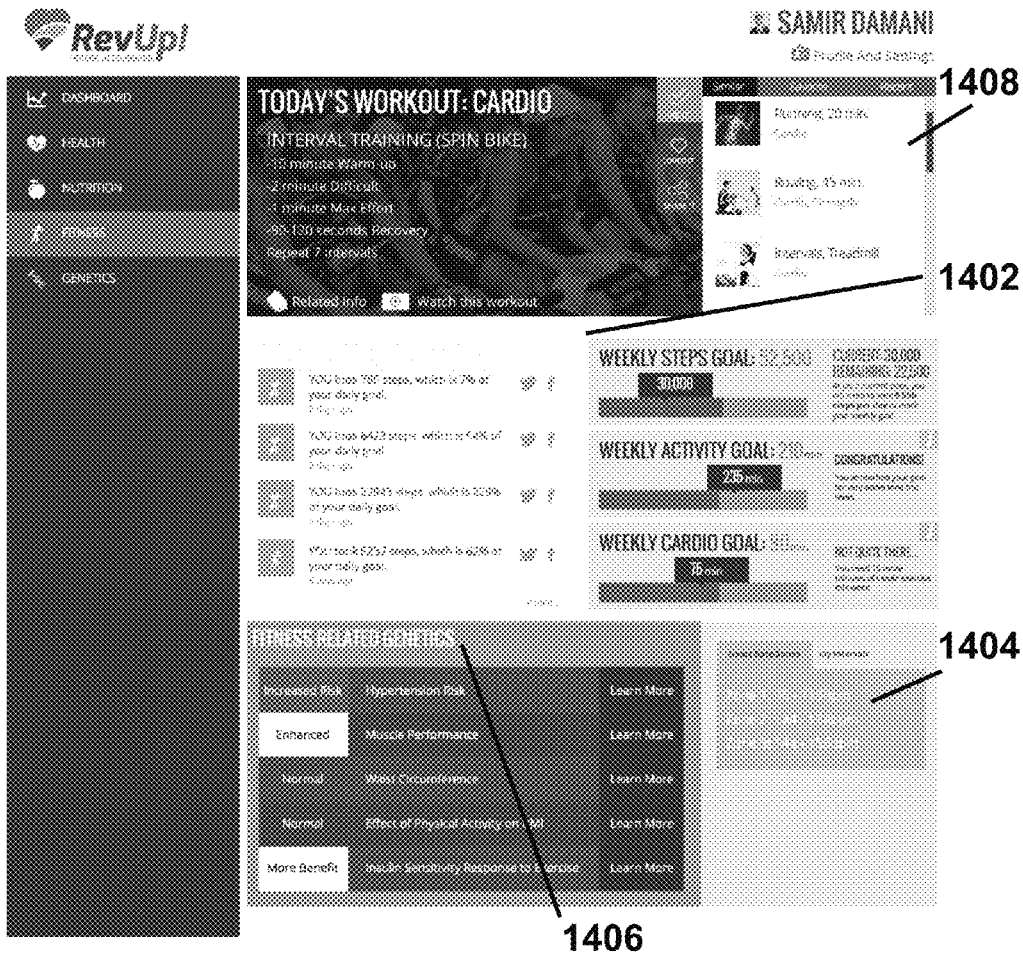
FIG. 14 is an illustration of a fitness dashboard interface, according to one embodiment of the invention.

FIG. 14 illustrates a fitness page 1400 of the dashboard interface which provides detailed graphical information on the user's fitness activity, such as steps, progress toward goals of activity and cardio exercise goals 1402, current interval levels 1404 for cardiac exercise and fitness-related genetic information 1406 that reminds the user of more specific goals that may have been developed based on the user's specific genetic profile. A primary goal of the fitness page is to help the user achieve a desired heart rate range for certain levels of activity, which will lead to improved RMR, VO2, metabolism and overall cardiac health. The user is also provided with suggestions 1408 for the types of activities that can be performed to meet fitness goals, such as spinning, rowing, treadmill, etc. The user can select certain activities as favorites and also review reports on their past activities. In one embodiment, the user can create a personal fitness goal, such as "running a marathon," after which the system will provide the user with a particular set of steps and goals to achieve in order to train for the marathon. The goals and steps may include desired RMR and VO2 levels, heart rate performance and recovery, nutrition and caloric recommendations along with balances of food types, etc.

Figure 15:
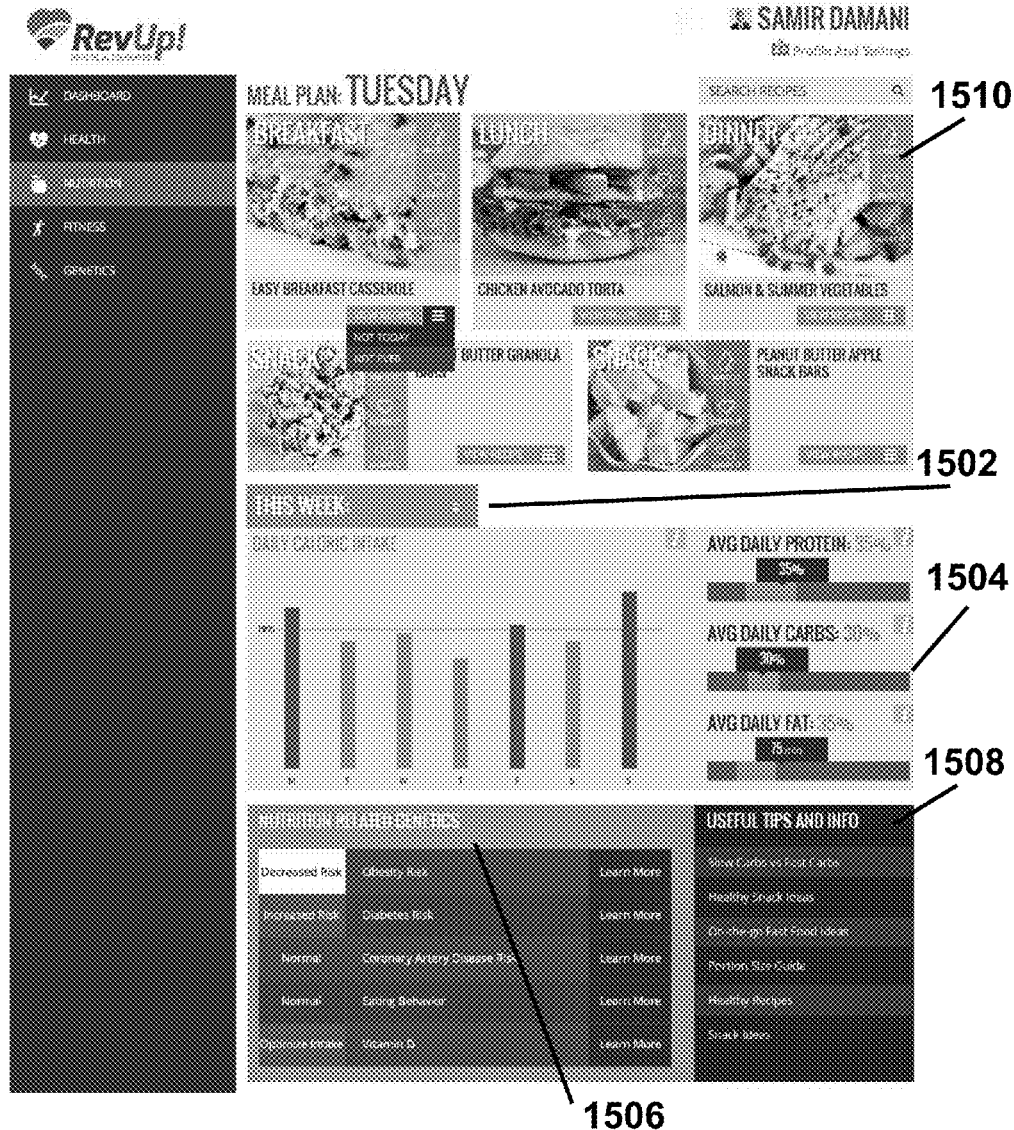
FIG. 15 is an illustration of a nutrition dashboard interface, according to one embodiment of the invention.

FIG. 15 illustrates a nutrition interface 1500 of the dashboard, which provides detailed information on the user's nutrition profile and data, such as caloric intake 1502, breakdown of food type 1504 (protein, fat, carbohydrate), nutrition-related genetic information 1506 and recommendations 1508 for food intake based on the user's profile and history. The nutrition dashboard may also provide a meal plan section 1510 which provides recommendations for different types of foods which meet the user's nutrition goals in terms of calories and food type. The user may be able to select certain foods as favorites and search for foods based on the food breakdown and calorie count. In one embodiment, the user can select a certain type of food if they end up consuming it and provide a review of the food or highlight it as a favorite for the future. The system may monitor user selections and develop a suggested food plan for the user and other users based on popular selections. The system may also provide recipes for the foods on the nutrition dashboard to help the user make the selected food.

The data collected can be displayed in a wholly interactive, customizable manner depending on each particular user and depending on the viewer who will be viewing the dashboard. In the embodiments illustrated in FIGS. 9-24, these reports may be customized for a user, a physician or healthcare team and even an administrator at a school or company who is managing a health incentives program. For example, a user with medical data indicating risk factors for chronic disease such as hypertension, hypercholesterolemia, coronary artery disease, cancer, diabetes, etc. may be categorized with specific goals to improve their mortality rates—such as nutrition and fitness recommendations, or in some cases, a recommendation to consult with a doctor to determine whether a certain disease is present.

The dashboard may also include a recommendations section which displays one or more recommendations to the user in order to help achieve one or more goals with regard to the user's health and wellness. The recommendations may be based on the user's profile and be updated based on current information that is periodically or constantly being input to the front-end cloud server by the third party data sources.

The dashboard may also include communication links where a user can communicate with a healthcare professional, nutritionist, fitness trainer, health coordinator, etc. to discuss the information on their dashboard and the recommendations being provided. The communication links may be links to separate user interfaces where the user inputs information and questions, a messaging tool where the user can send an e-mail, text message or other type of electronic message, or even a link to an audio or video application where the user can communicate with another party by voice, video or both.

The dashboard may also have a general notifications section where the user can be provided with one or more notices regarding their profile, needed actions or messages from an administrator, etc. In one embodiment, the user may be asked to visit a clinic to complete a genetic profile test or upload new data from one or more wireless health devices so that the user's dashboard may be updated.

In one embodiment, the dashboard may provide one or more information tabs where different classes of information may be grouped together in a more detailed dashboard for a particular category of information. In one embodiment, the tabs may correspond to health, nutrition, genetics and fitness. By selecting one of these tabs, a new dashboard is displayed with information specific to one of these categories, allowing the user to see a more detailed breakdown of information in this category that might not otherwise be displayed on an overall dashboard overview. The information tabs may also pertain to messaging, notifications, incentives and rewards, syncing with wireless health devices, etc.

The type of data collected and displayed on the dashboard may relate to any component of a user's genetic profile, medical information or history, fitness and nutrition. Examples of this data include heart rate, blood pressure, cholesterol, obesity, resting metabolic rate (RMR), oxygen consumption (VO2), weight, body fat, visceral fat, muscle mass, body water, bone mass, blood glucose, sleep data, caloric intake, fat intake, vitamin intake, calories burned, fat burned, steps taken (pedometer).

FIG. 9 illustrates one embodiment of a health and wellness graphical user interface (GUI) dashboard which lists a plurality of physiological data, including blood pressure, weight, total cholesterol, inflammation, body fat percentage, and sleep quality. Some of this information is displayed in graphical form to show historical data over a period of time, helping the user determine if they are moving in a certain direction. For example, the user in FIG. 9 is making progress in losing weight, while the blood pressure chart indicates that blood pressure is increasing. Some information may be displayed using color-coded graphical information, such as a yellow-colored bar for the total cholesterol level of 220 that is considered potentially unhealthy. In contrast, the indicator for inflammation is a green bar, as the measured level (1 mg/L) is within healthy levels.

The dashboard may also display one or more notifications to the user about the measured levels. In the dashboard in FIG. 9, this user is given warning notifications about their high cholesterol levels, high blood pressure and obesity. These notifications may be based on currently measured levels of these indicators or on genetic profile information that indicates a predisposition to one or more of these conditions. The dashboard in FIG. 9 also displays a notification that the user's dashboard is incomplete since it is missing one or more items related to the user's genetic profile, medical history, fitness or nutrition. The user may be provided with a hyperlink on the notification where steps can be taken to complete the missing items, such as scheduling an appointment with a clinic to finalize a genetic test or syncing data from a wireless health device with a computer in order to update the information on the dashboard.

The dashboard may display a global summary of the user's health and wellness as a summary or home screen, but may also provide more specific dashboard GUIs specific to one type of information, such as nutrition, genetics (DNA), fitness and challenges. The challenges dashboard GUI may provide one or more activities in which the user can participate.

FIG. 10 is an illustration of a GUI of an overall health and wellness dashboard which provides a summary of information from several different categories, including physiological data, fitness data, nutrition data and genetic information.

Specifically, FIG. 9 provides a chart with a Nutrition Overview indicating a breakdown of the levels of fat, sugar, carbohydrates and protein in the food consumed by the user over a period of time. A genetic report table may also list one or more suggestions for the user based on information obtained from the user's genetic profile, including nutrition advice, fitness advice and warnings about susceptibility to weight gain or certain diseases such as diabetes.

Health Alerts

Figure 16:
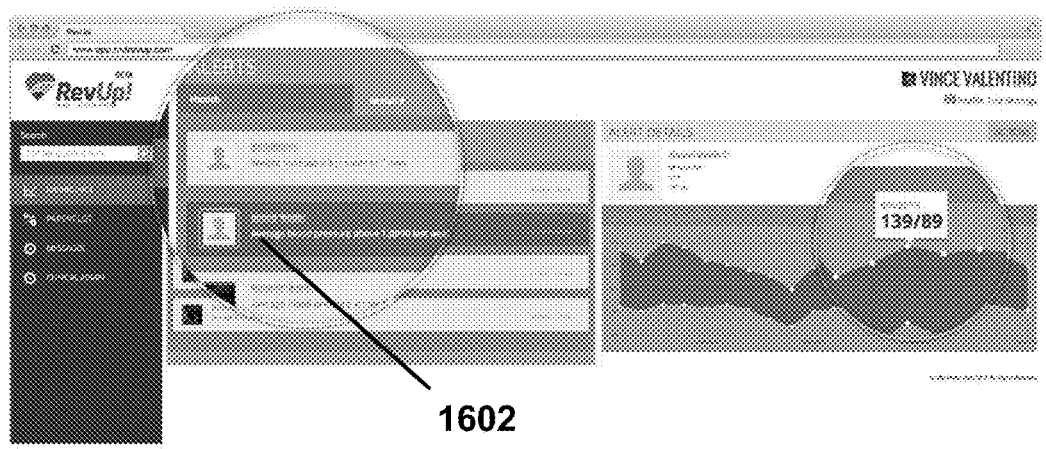
FIG. 16 is an illustration of an alerts interface, according to one embodiment of the invention.
Figure 17A:
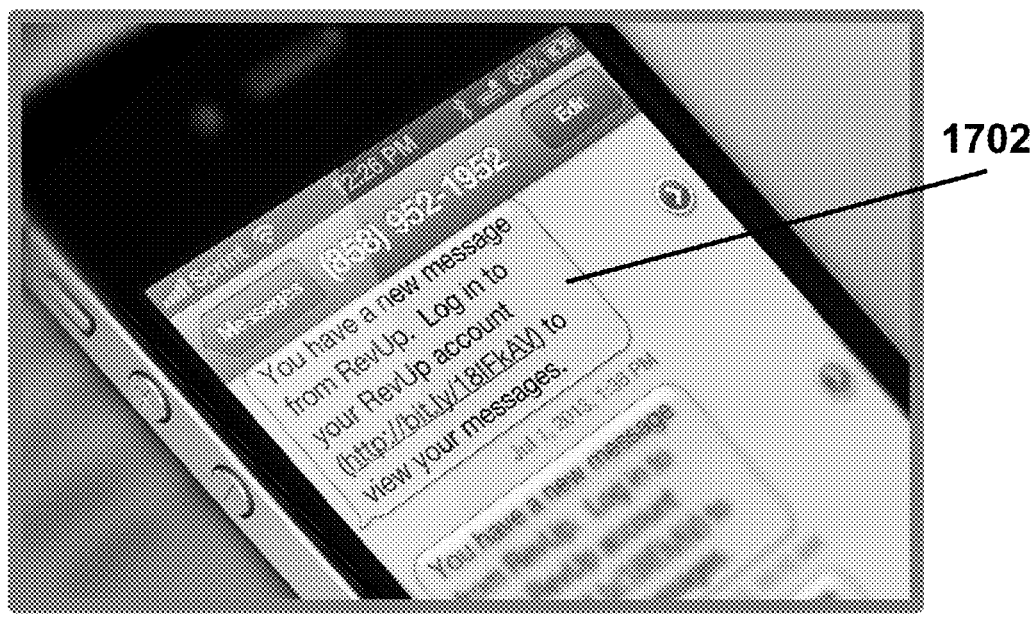
FIGS. 17A and 17B are illustrations of a notification displayed on a portable electronic device, according to one embodiment of the invention.
Figure 17B:
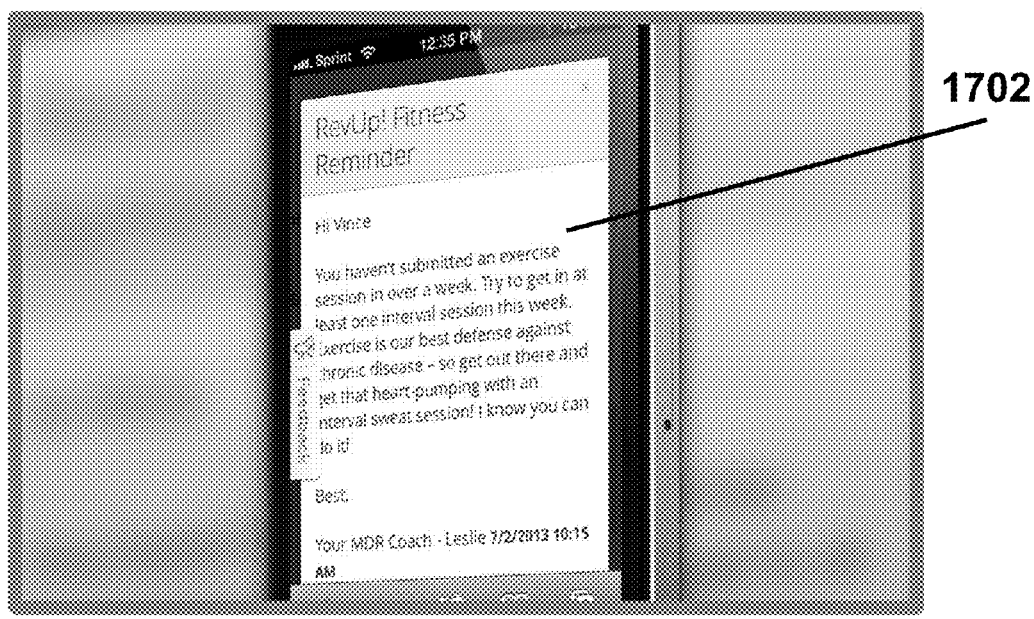

The user may also receive one or more health alerts either through the dashboard 1600, as illustrated in FIG. 16, or via a separate messaging protocol 1700 (SMS/MMS text messages, e-mails, etc) on the user's portable electronic device, as illustrated in FIG. 17. The alerts 1602 may tell the user that they haven't met one or more goals related to a level of fitness or nutrition or a physiological measurement related to cholesterol, body composition or blood pressure, etc. The health alerts may be tiered based on the importance of the alert or the history of response from the user. In one embodiment, a tier one health alert will be a message 1702 sent from the dashboard, while a tier two health alert is a call from a health coach, physician or other healthcare team member. A tier three health alert may be an appointment (in person or virtually) with a physician or other healthcare team member to discuss specifics of the user's health.

As illustrated in FIG. 17, the alerts and notifications may also simply tell the user that they have received a message or notification from their system and provide them with a link to their dashboard in order to prevent transmitting any private medical or health information about the user.

In one embodiment, the health alert may be customized for a particular user based on the genetic, medical, fitness and nutrition information obtained for that user. For example, a tier one alert may be generated if the user does not have a certain minimum heart rate for a certain period of time (which would be indicative of exercise). In another embodiment, the user may receive a tier one alert if they gain more than 2 pounds in a week, or 5 pounds in a month. Similar alerts may be generated for levels of blood pressure, a number of steps taken, a number of calories consumed, etc.—basically any measured value relating to health, fitness and nutrition. These alerts let the user and the user's healthcare professional know that their health and wellness goals are not being met.

Incentive Alerts

In one embodiment, the user may receive "incentive alerts" if certain levels of health, fitness or nutrition are achieved based on goals that are customized for each user. For example, a reward may be provided to the user if they walk a certain amount over a given period of time, lose or maintain a certain amount of weight, reduce their blood pressure to a certain rate, etc. As with the health alerts, the incentive alerts can be set up for any measured value relating to health, fitness and nutrition. The incentives may also be customized for each user, for members of a certain group (employees of a company), or based on user-selected preferences for rewards (monetary, lifestyle, recognition, etc.). Although the incentives may be explicitly shown on the dashboard, in one embodiment, the incentives may be provided to a user separately from the dashboard, such as by offering a user lower health insurance premiums if they enroll in a program with the dashboard and meet certain goals relating thereto.

Additional features of the incentives, as well as a points and rewards system, are described further below.

Group Reports

Figure 18:
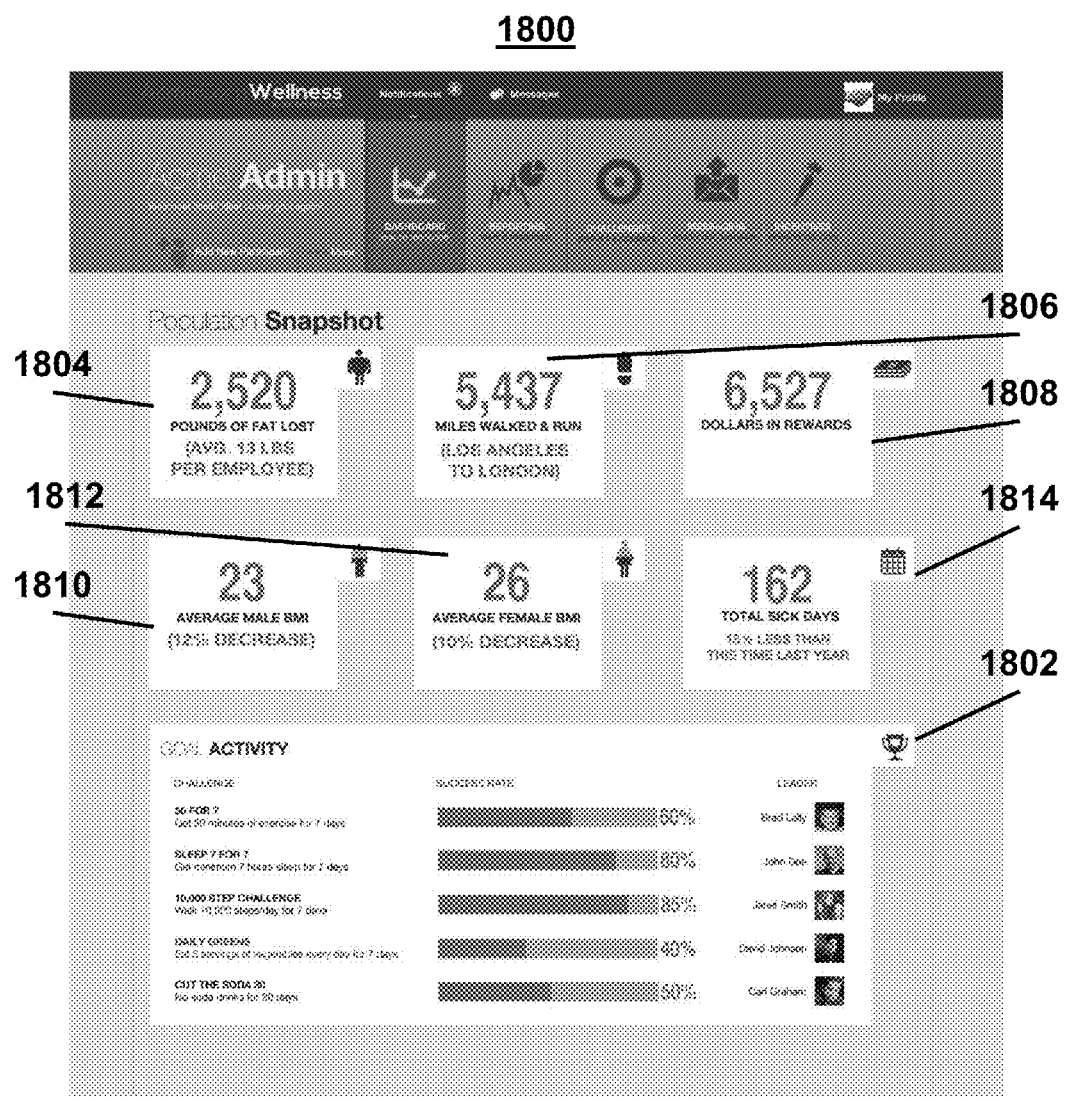
FIG. 18 is an illustration of a GUI of a group health and wellness dashboard illustrating a plurality of information aggregated for a group of people; according to one embodiment of the invention.

FIG. 18 is an illustration of a GUI 1800 of a group health and wellness dashboard illustrating a plurality of information aggregated for a group of people; according to one embodiment of the invention. The group report may display overall health and wellness information 1802 for a group of people, such as employees in a company. The group dashboard in FIG. 16 may therefore display overall averages of information, such as total weight lost by the group and an average weight loss per person 1804, a total distance run 1806, the amount of incentives and rewards 1808 provided to the group of users, the average male BMI 1810 and female BMI levels 1812, and even a total amount of sick days 1814 accrued by the group along with a comparison to previous levels. A group administrator can therefore view the details and historical levels of the group, including the goals, to determine if the group is making progress and if certain incentives are effective.

Healthcare Professional Dashboard

Figure 19:
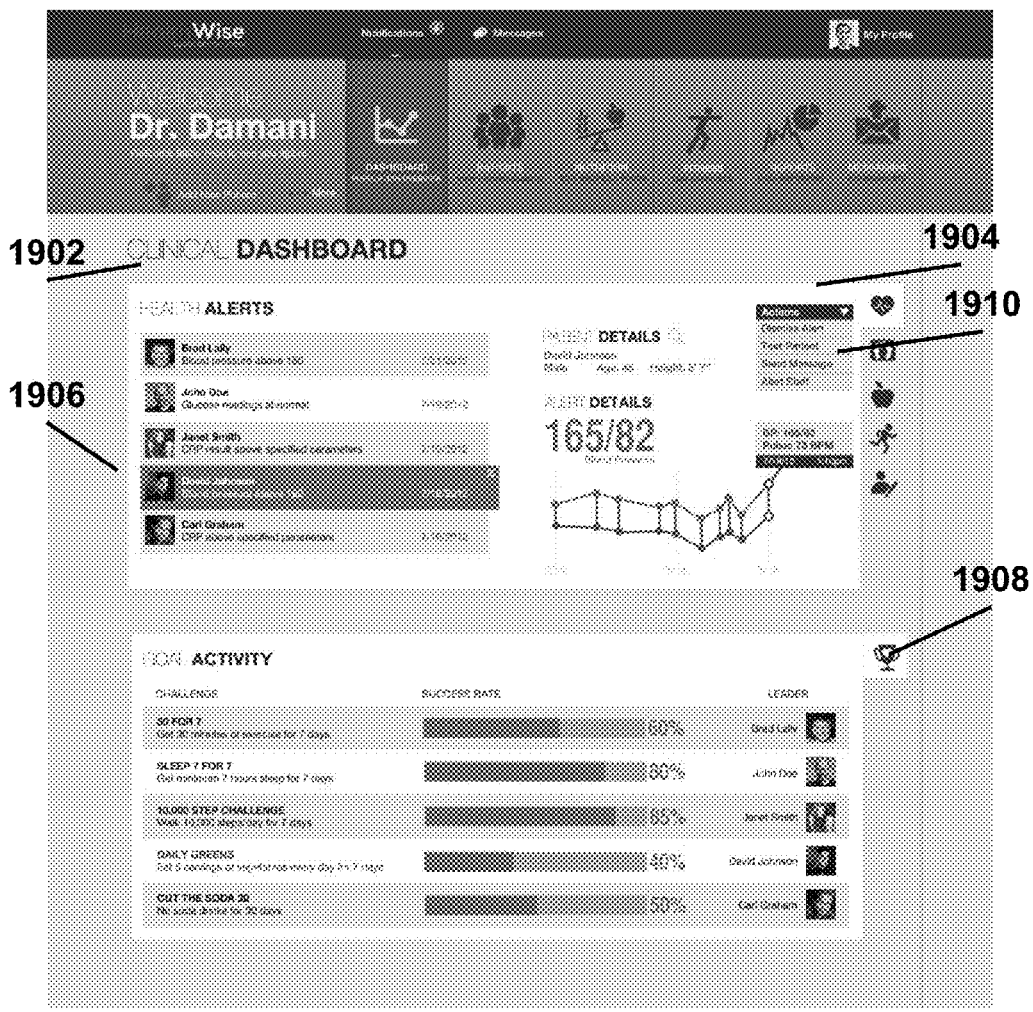
FIG. 19 is an illustration of a GUI of a clinical dashboard for use by a medical or healthcare professional in evaluating the health and wellness of one or more users, according to one embodiment of the invention.

FIG. 19 is an illustration of a GUI of a clinical dashboard 1900 for use by a medical or healthcare professional in evaluating the health and wellness of one or more users, according to one embodiment of the invention. The healthcare professional dashboard may include a list of patients 1902 for whom the healthcare professional is responsible along with an overall summary 1904 of each patient's information, including a list of "health alerts" 1906 for users which are assigned to a particular healthcare professional. The progress 1908 of each user toward particular goals and charts and graphs of data relating to fitness and nutrition information may be displayed to the healthcare professional, along with options to obtain more detailed information on a particular user and the user's profile. Other options on the healthcare professional dashboard include the ability to communicate 1910 with each user or group of users using a built-in messaging tool (described above), a section displaying all health alerts, a section displaying notifications, a section displaying user progress toward goals, etc. The healthcare professional dashboard may also provide options for adding and enrolling new users and managing user accounts.

The healthcare professional dashboard may also provide analytical tools that help a healthcare professional analyze data from one or more users and attempt to correlate data to determine if goals and recommendations should be changed or modified. The goals and recommendations may be customized for each user by the healthcare professional or provided to an overall group of users who exhibit similar profiles.

Figure 20:
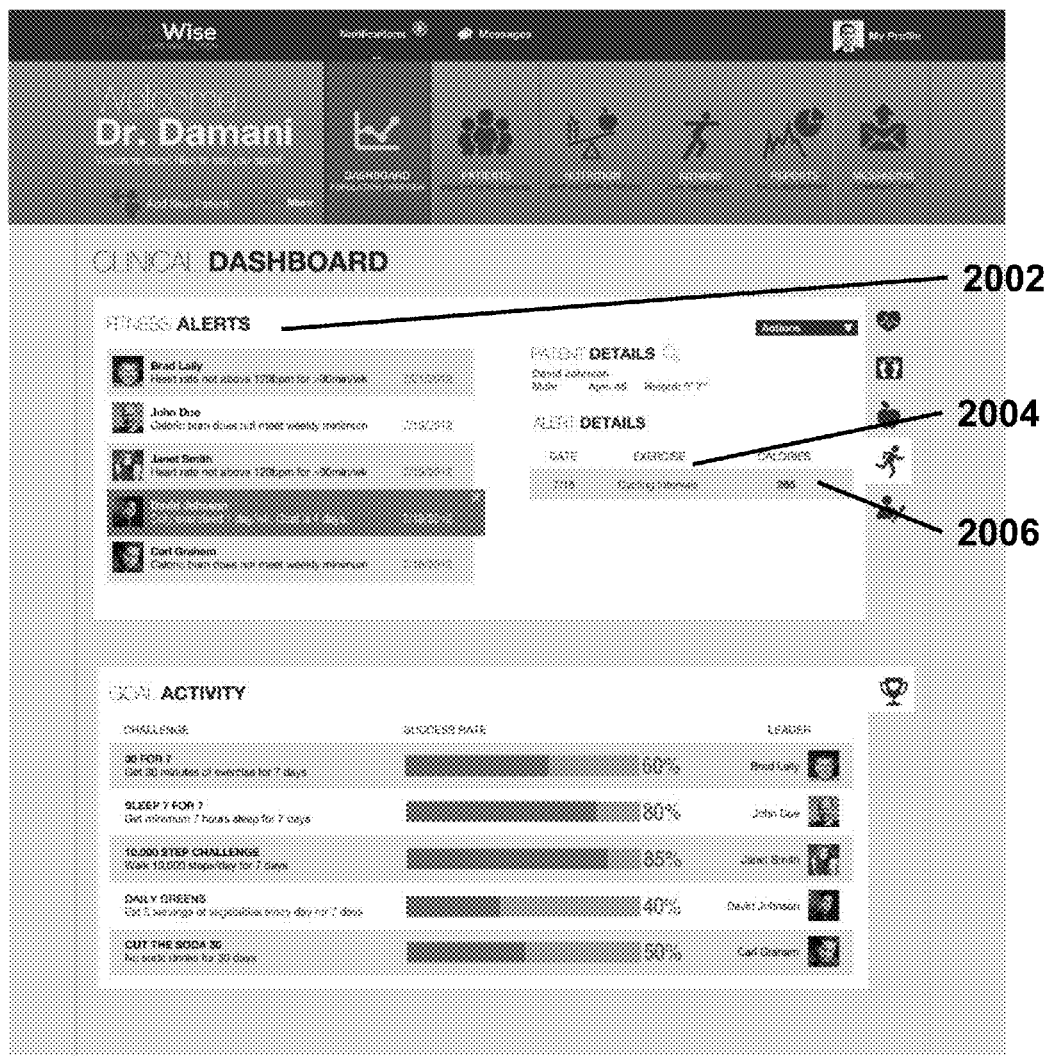
FIG. 20 is another illustration of the GUI of the clinical dashboard with a plurality of notifications for the one or more users, according to one embodiment of the invention.

FIG. 20 is another illustration of the GUI of the healthcare professional dashboard 2000 showing fitness alerts 2002 with detailed user profile information on a user's recent exercise regimen 2004, the type of exercise completed and the number of calories that the user burned 2006.

Figure 21:
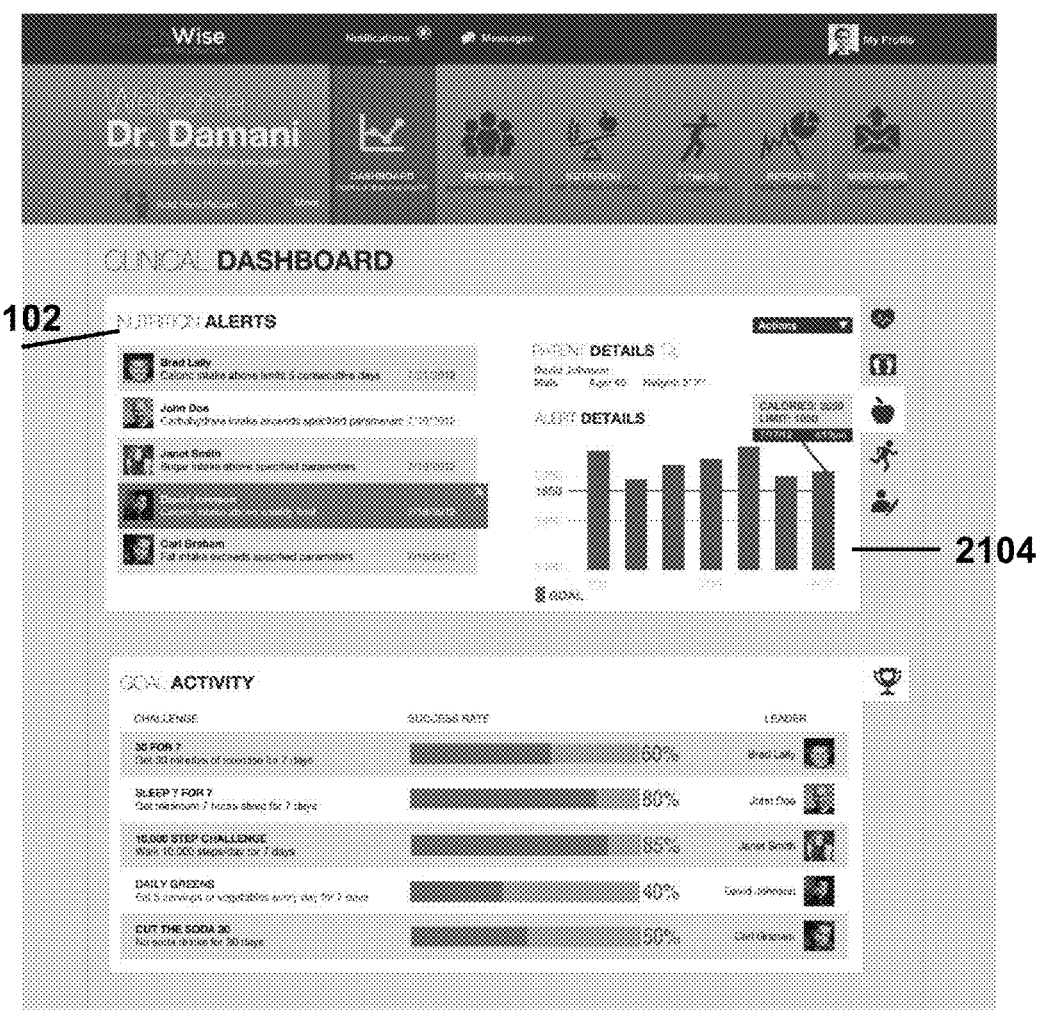
FIG. 21 is another illustration of the GUI of the clinical dashboard with additional nutrition information displayed for one or more users, according to one embodiment of the invention.

FIG. 21 is another illustration of the GUI of the healthcare professional dashboard 2100 displaying a list of nutrition alerts 2102 with a chart 2104 of caloric intake for a particular user over several days. The healthcare professional can see whether the user has met or exceeded a specified number of calories consumed per day and then follow up or issue an alert to the user that they are not meeting a goal of minimizing calorie consumption over a period of time. If the alert is automatically sent by the dashboard to the user, the healthcare professional may also receive the alert in the fitness alerts window and then view the detailed information to see why the user is receiving the alert.

Figure 22:
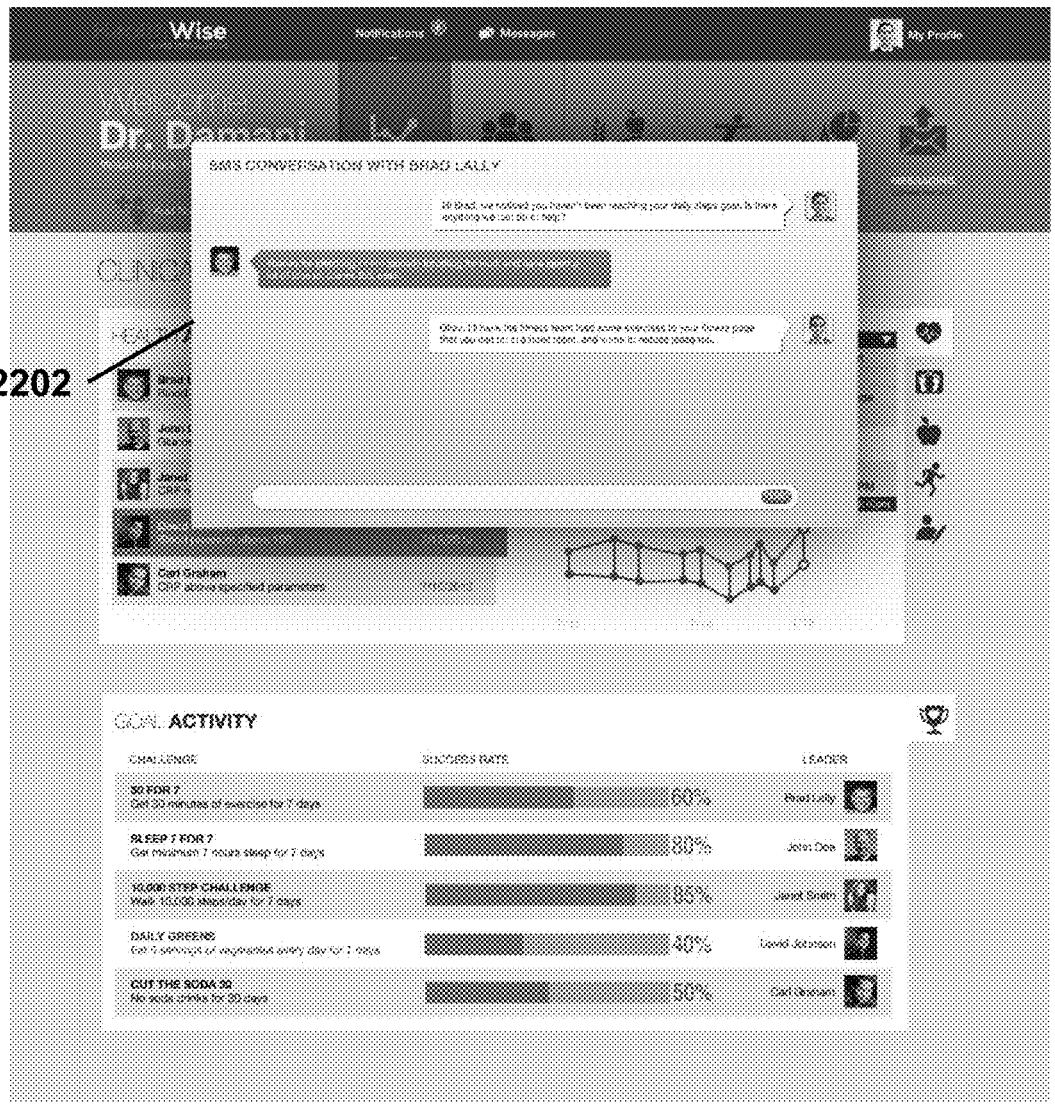
FIG. 22 is an illustration of a GUI of an interactive messaging service integrated into the health and wellness dashboard for communication between the user and the medical or healthcare professional.

FIG. 22 is an illustration of a GUI of an interactive messaging service 2200 integrated into the health and wellness dashboard for communication between the user and the healthcare professional. In this illustration, the healthcare professional can select an option on the dashboard to send a message to the user, which opens a new messaging window 2202 where the healthcare professional can communicate with the user to discuss their progress (or lack thereof) toward one or more goals. The messaging protocol may be any known communication medium, such as text (SMS or MMS), e-mail, instant messaging, video or audio calls, etc.

Figure 23:
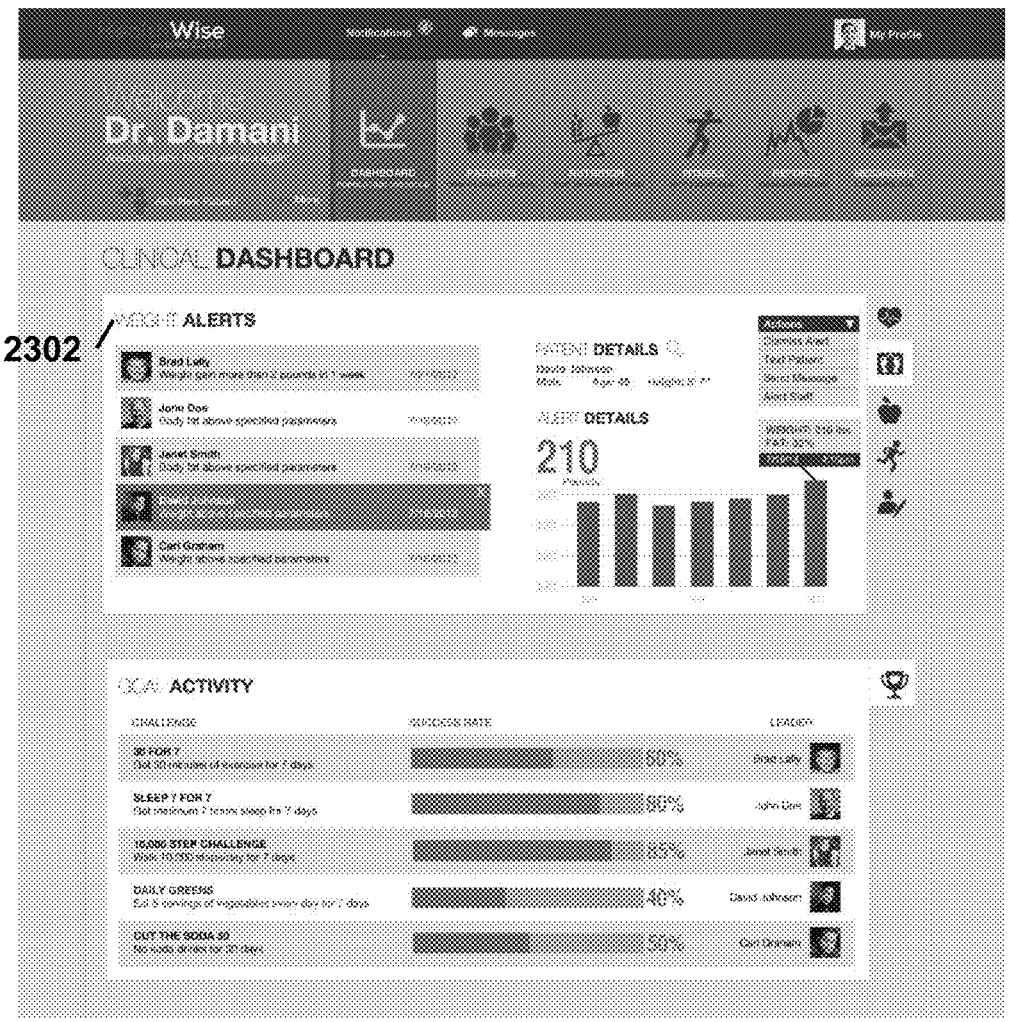
FIG. 23 is another illustration of the GUI of the clinical dashboard with additional health information displayed for one or more users, according to one embodiment of the invention.

FIG. 23 is another illustration of the GUI of the healthcare professional dashboard 2300 with a weight alerts window 2302 displayed for one or more users.

Grading

The patient's progress toward their health goals may be evaluated by measuring the same parameters measured during the initial assessment phase and then determining a grade, such as a letter or numerical value which indicates the patient's progress or achievement of their goals at any point during the patient's participation. In one embodiment, the user is graded on the same values described above with regard to their assessment, including their RMR level, Body Fat Percent, Visceral Fat and VO2, as indicated in Tables 1-11 immediately below:

TABLE 1

Resting Metabolic Rate - ml/kg/min

| Grade | Goal |
|---|---|
| A >4.51 | |
| A− 4.26-4.50 | 5% increase |
| B+ 4.01-4.25 | 10% increase |
| B 3.50-4.0 | 15% increase |
| C+ 3.25-3.49 | 20% increase |
| C 3.0-3.24 | 25% increase |
| C <2.9 | 30% increase |

TABLE 2

Body Fat Percent

| Percent | Goal Male | Goal Female |
|---|---|---|
| C 50-40% | 50% decrease | 40% decrease |
| C+39.9-35% | 40% decrease | 30% decrease |
| B−34.9-30% | 35% decrease | 25% decrease |
| B29.9%-25% | 30% decrease | 20% decrease |
| B+24.9%-20% | 25% decrease | 10% decrease |
| A−19.9-16% | 20% decrease | 5% decrease |
| A15.9-10% | 15% decrease | 0% decrease |

TABLE 3

Visceral Fat

| lb. | Grade | Goal |
|---|---|---|
| >40 lbs. | C | 50% decrease |
| 35-35.99 | C | 50% decrease |
| 30-34.99 | C+ | 45% decrease |
| 25-29.99 lb. | B− | 45% decrease |
| 20-24.99 lbs. | B | 40% decrease |
| 15.0-19.9 lbs. | B+ | 30% decrease |
| 10.0-14.9 lbs. | A− | 20% decrease |
| <9.9 | A | |

TABLE 4

VO2 - ml/kg/min

| Grade | Goal |
|---|---|
| A >53 | |
| A− 49.9-52.9 | 5% increase |
| B+ 45.0-49.9 | 10% increase |
| B 40.0-44.9 | 15% increase |
| B− 35.0-39.9 | 20% increase |
| C+ 31.0-34.9 | 25% increase |
| C 25-30.9 | 30% increase |
| C <24.9 | 35% increase |

TABLE 5

Caloric Guidelines - (REE = Resting Energy Expenditure) Weight Loss range

Top caloric intake = REE Peak exercise days
Average caloric intake = REE - 15% Medium intensity exercise day
Minimum caloric intake = REE - 20% Non exercise day

TABLE 6

Maintenance intake range

Top caloric intake = REE × 20%, Peak intensity days
Average caloric intake = REE × 10%, Medium intensity days
Minimum caloric intake Grading System .docxREE

TABLE 7

Bone Mass

A = above average bone mass
B = average bone mass
C = below average bone mass

TABLE 8

Male - Average

Weight Less than 143 lb., 5.9 lb
Weight 143-200, 7.3 lb.
Weight 200-up, 8.1 lb.

TABLE 9

Female Average

Weight Less than 110, 4.3 lb.
Weight 110-165, 5.3 lb.
Weight 165-up, 6.5 lb.

TABLE 10

Posture/Core

A = All 5 kinetic chain check points satisfactory
B = 4 satisfactory kinetic check points
C = 3 or fewer satisfactory check points

TABLE 11

Definition of grades

C = Health Alert, high importance to improve
B = Satisfactory but health potential not achieved
A = Full Health Potential has been achieved Each individual parameter may have customized levels based on the significance of each parameter to the user's overall health, and the grades for each parameter may be used individually, to provide the user with a more detailed assessment of their health, or together (such as by averaging the grades for all parameters) in order to provide the user with an overall assessment of their health. As indicated in Table 11, the grades (letter or numeric) may have specific meaning with regard to action items that the user needs to complete. The goals may be set based on levels of each parameter which are generally considered in a healthy range for all humans, or which are customized for the particular user based on their initial assessment and continuously-updated assessments.

Points and Rewards

In one embodiment, a points system may be implemented where users earn points for various activities and levels of participation, achievement of intermediate and overall goals of the program, and other activities that would benefit from incentivizing. The points may be used to compete against other users in a game to provide motivation via competition, or to earn rewards that will further motivate them to continue participation. The points system is designed to accomplish two goals: motivating participants to engage in healthy activities and providing a reliable metric for users, health care provider and organizations administering and subscribing to the system to track user participation.

Figure 24:
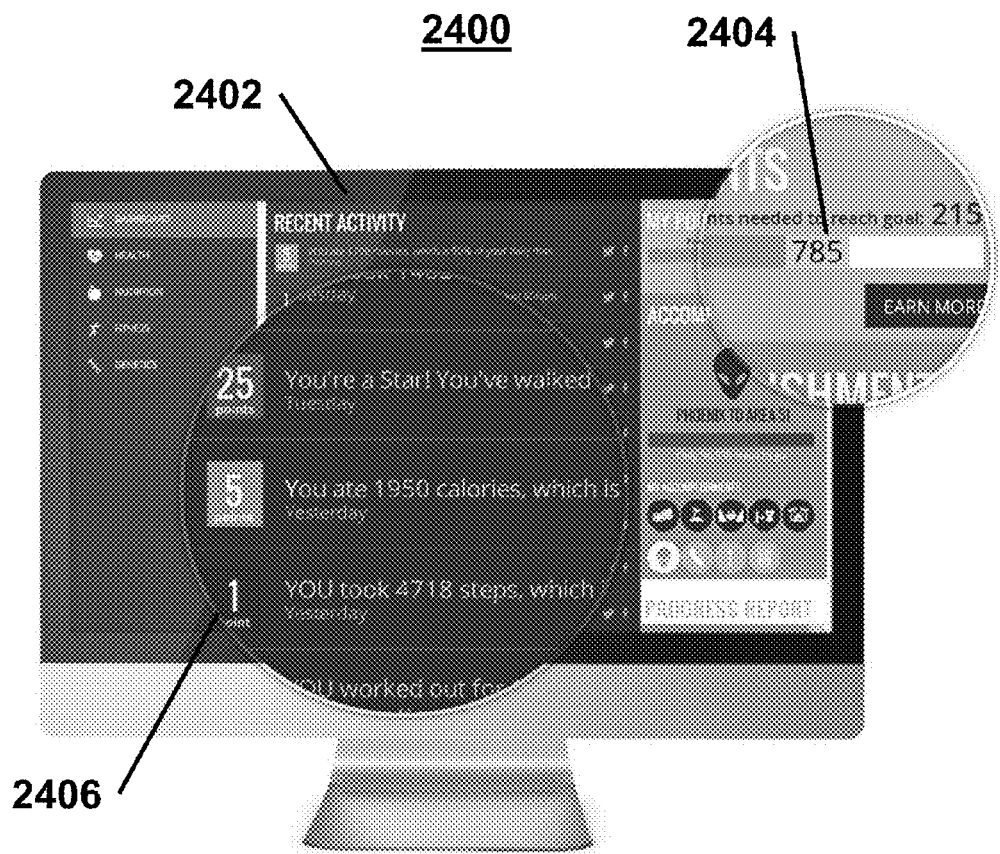
FIG. 24 is an illustration of a points activity interface, according to one embodiment of the invention.

The points system may be integrated into the overall dashboard and user interface 2400 so the user sees the points they earn for each activity and goal, as shown in FIG. 24. The Recent Activity feed section 2402 displays the points 2404 associated with all the health-related activity of the participant so they can see the reward from their activities in real-time. Points may be weighted so that actions with higher impact on health and/or greater levels of participation receive more points. Participants can then see which activities 2406 provide more points, thus motivating them to engage in those healthy behaviors more frequently.

Users can earn points every time they track their activity, exercise, food intake, blood pressure and other metrics. Additional points may be awarded with a participant achieves a health goal or milestone. The system allows providers to decide what levels of participation they would like to set for their users to receive rewards and incentives, which may be tied to the overall goal of the provider or organization.

FIG. 25 illustrates a table with one embodiment of a points system which rewards points to users based on recording activity with an activity tracking device (such as a Fitbit), taking a certain amount of steps per day, an amount of heavy activity per day, recording the user's weight with a scale, logging food and achieving specific overall step goals. Different Groups A, B and C may be created based on different levels of participation within the system, such that some groups may not participate in certain activities and tracking A threshold value may be provided within each activity that defines a minimum amount of the activity that will earn the points. For example, in order to earn points for logging food each day, the user must log at least 500 calories worth of food. An additional threshold value may be provided, as indicated in the far right column, which provides the maximum value of points that can be earned for a particular activity over the course of the program. Providing intermediate awards and points will help motivate users along the way and help users who may not achieve a reward in one month to work toward a reward in a subsequent month.

FIG. 26 illustrates an outcome-based points system which awards points based on achieving certain outcomes or progress toward an outcome, such as a desired RMR, visceral fat, body fat, VO2 or HbA1c. In this embodiment, the points are awarded as a percentage of the user's achievement of the outcome, such that a user who attains 90% of their set RMR goal will obtain 90% of a total of 250 possible points. These points may be awarded at various assessments during the program as well as at the end of the program.

FIG. 27 illustrates possible incentives and rewards that may be provided to the various Groups by each program sponsor or provider. The incentive design refers to whether the incentive is designated for a specific individual user or a group of users based on group achievement. For example, in FIG. C, the Group C (Example 3) may be provided with a group-designed incentive based on an arrangement of 14 groups of 5 people who are all blindly participating in the groups. An incentive, such as cash, may be awarded to the individuals that hit their thresholds within each group, where the cash award is divided by the winners on a monthly basis. Other incentives include fitness devices, exercise equipment or activity tracking devices to further motivate the user to participate in the program. As illustrated in the right column, another option is to provide awards to top improvers and point gainers in order to motivate users who may have more difficulty achieving the goals.

FIG. 28 illustrates several additional activities that may be incentivized through points and rewards. For example, activities that could earn points include logging blood pressure, attaining a threshold value of very active minutes, recording interval training sessions with a heart rate monitor, taking a blood glucose reading (i.e. for a diabetic), consecutive days of food logging or logging 90 minutes of exercise over a 3 day period. The point values and thresholds for each of these activities may be customized as needed in order to provide the right amount of incentivizing to certain groups of users.

VII. Outcomes

Over ninety percent of patients participating in the embodied methods experienced statistically significant improvements in resting metabolism, body fat, visceral fat reduction and improvements in cardiorespiratory fitness.

FIG. 29 is a table illustrating measured physiological changes in a set of patients using the systems and methods described herein over a period of time. The table illustrates changes the various physiological parameters on a per-day value, and also rates the statistical significance of the results (p-value) for the overall change in a parameter. A p value of less than 0.05 generally means that there is a statistically significant improvement in that individual parameter. The table also indicates the statistical significance of age and sex on the changes observed for each value amongst the group of patients. As shown in the table, almost all measured parameters changed over the course of the program. Age was not a factor in influencing a patient's response to the program, although sex (gender) had some influence on patient response to some of the parameters. The measurements of VO2, RMR and decreases in visceral fat are tightly linked to reduced death, and are considered key performance metrics.

Figure 30:
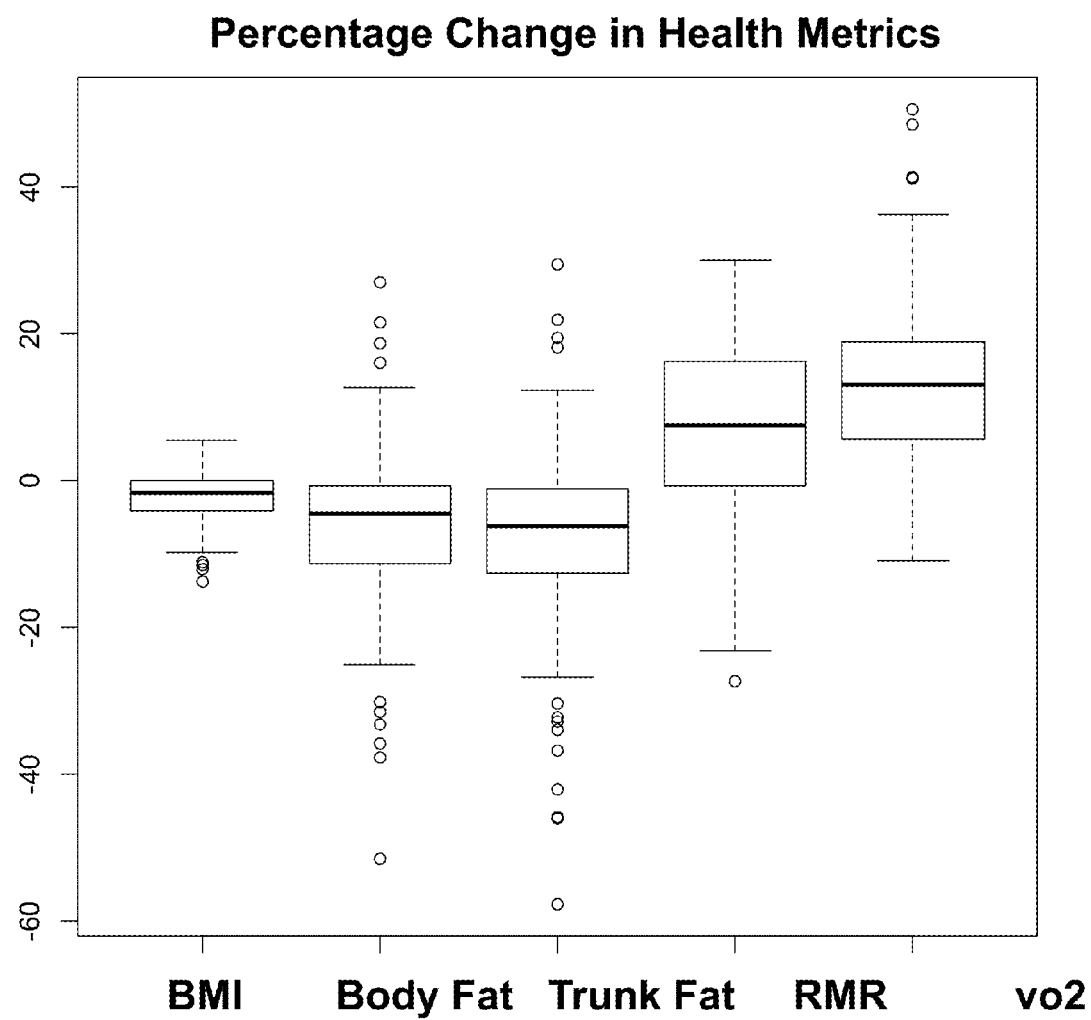
FIG. 30 illustrates the overall statistical change in numerous health metrics, including BMI, body fat, trunk fat, RMR and VO2.
Figure 31:
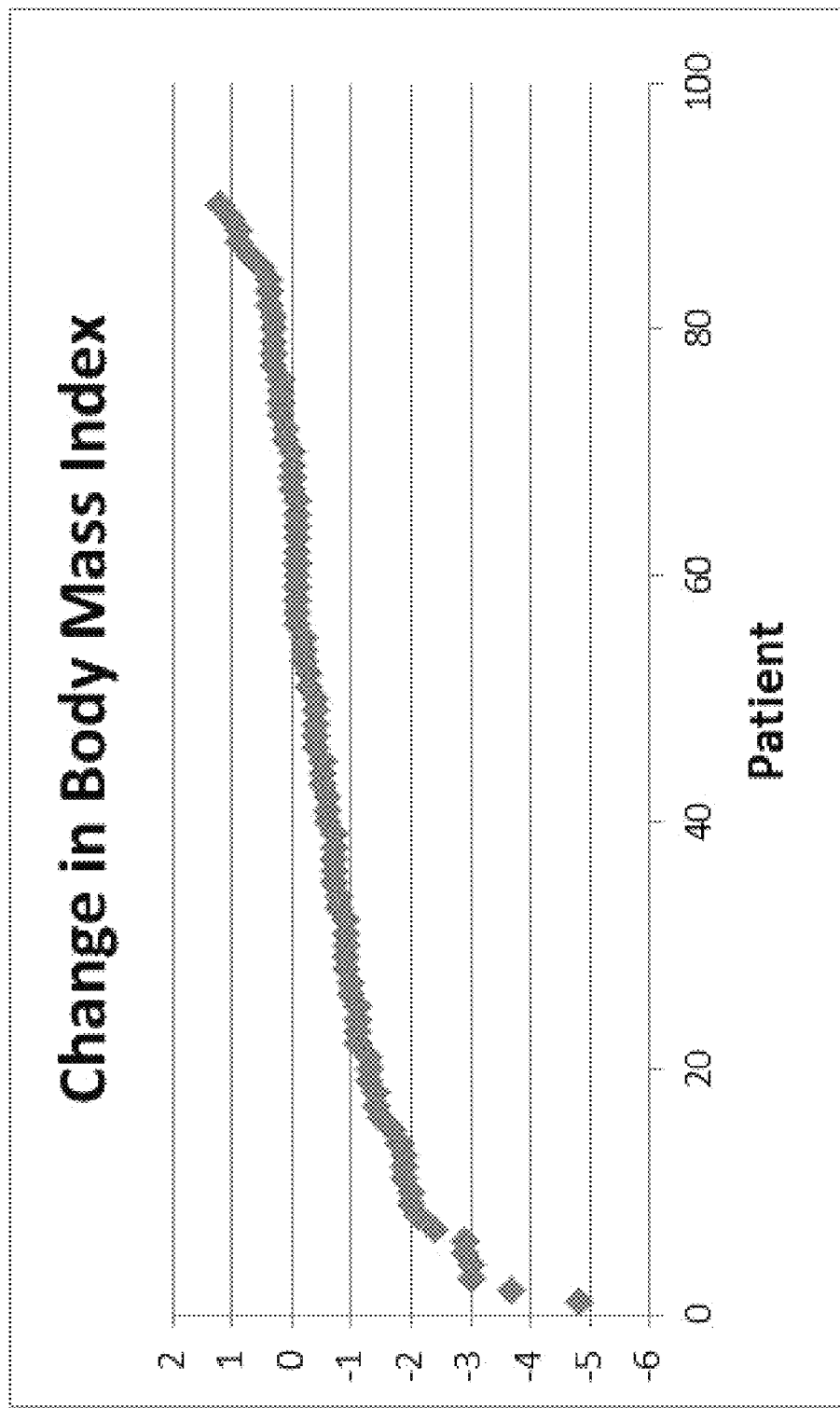
FIG. 31 illustrates the change in BMI.
Figure 32:
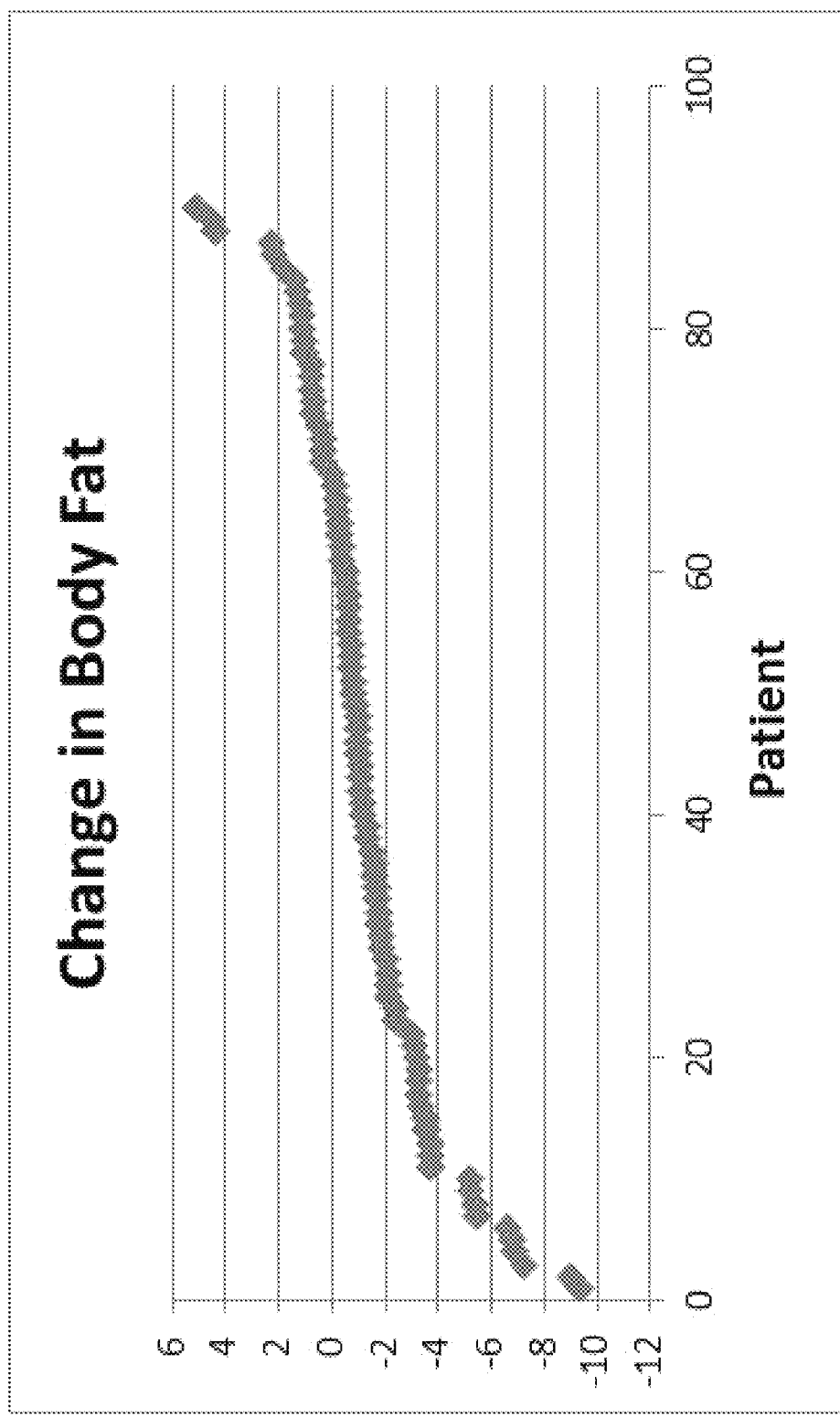
FIG. 32 illustrates the change in body fat.
Figure 33:
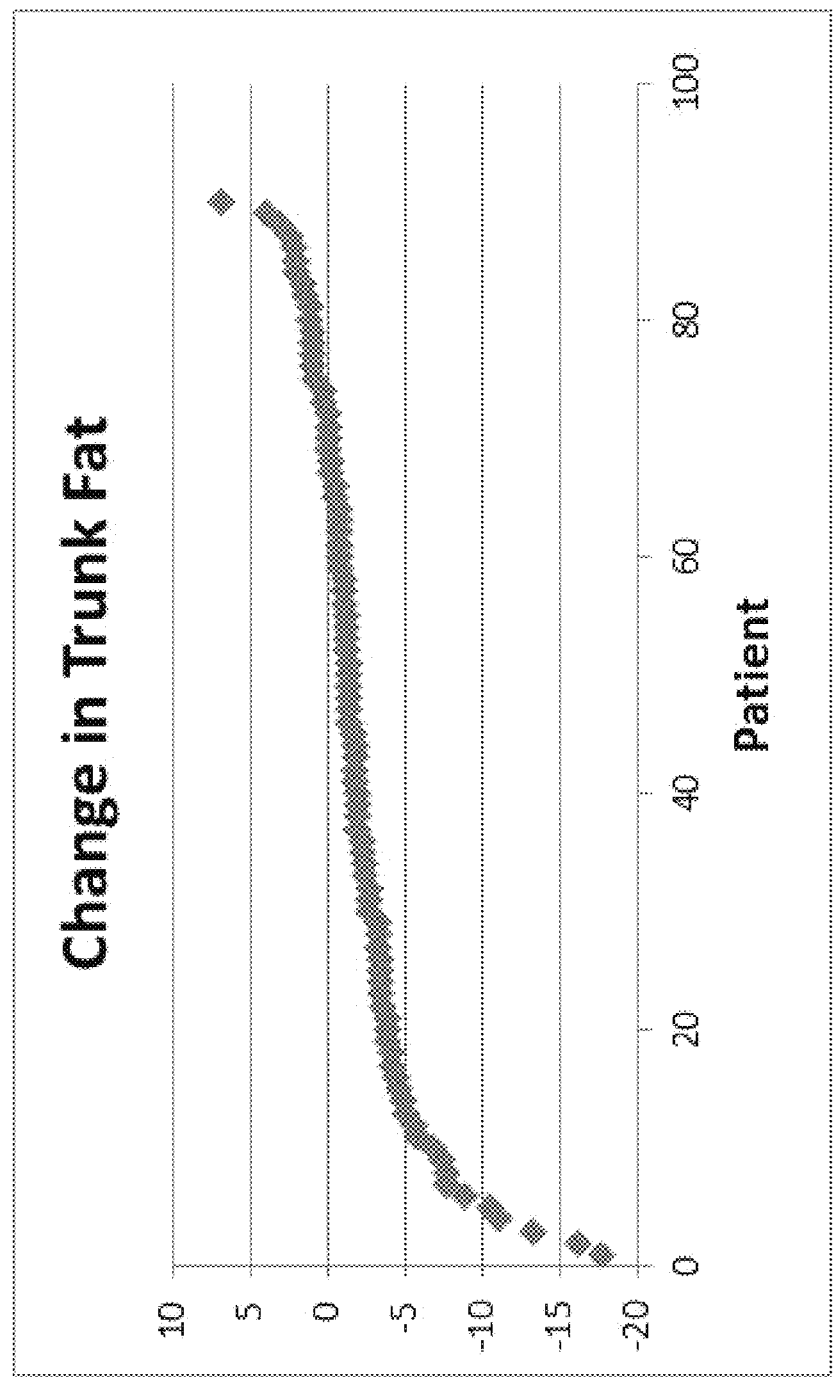
FIG. 33 illustrates the change in trunk fat.
Figure 34:
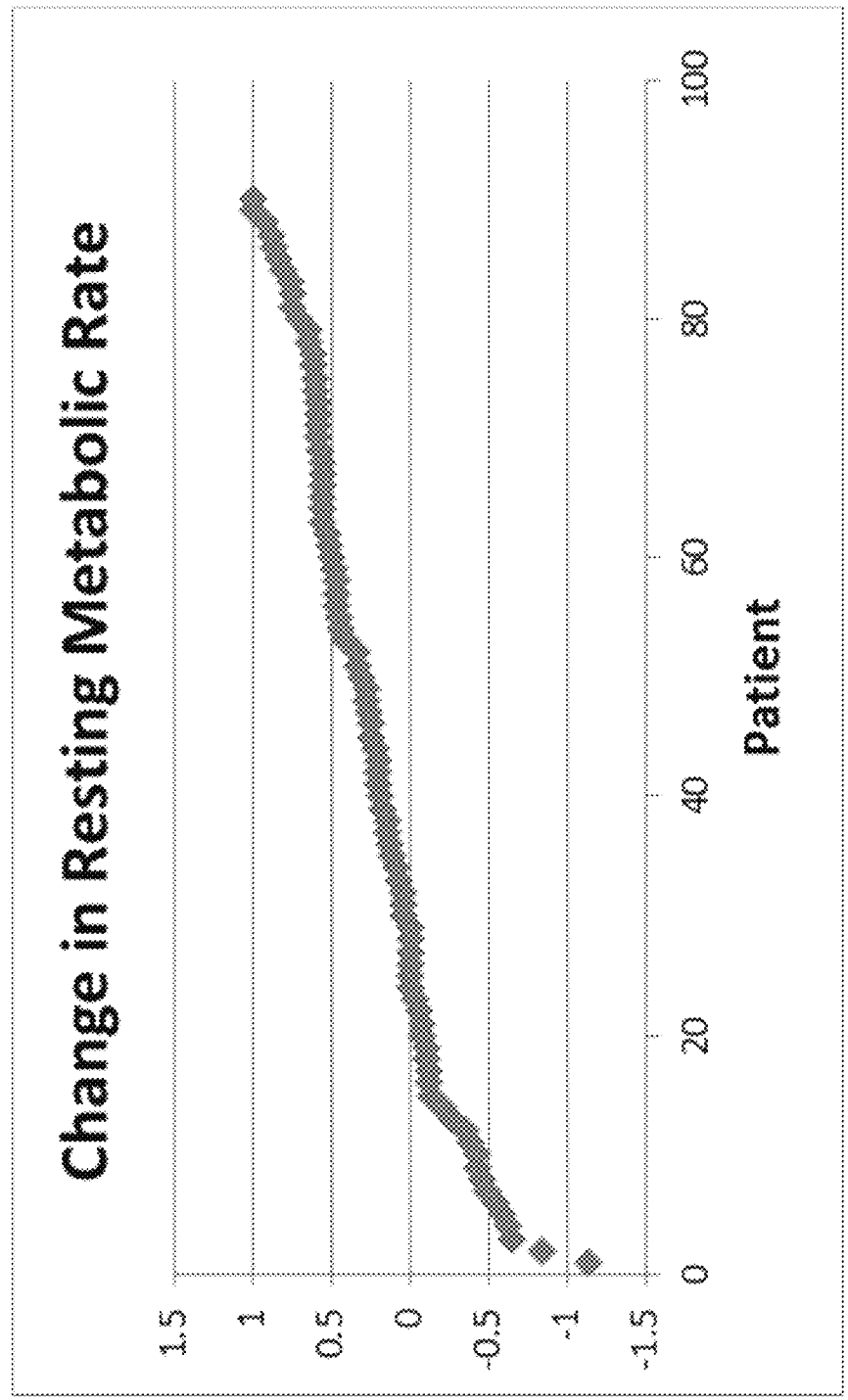
FIG. 34 illustrates the change in resting metabolic rate (RMR)
Figure 35:
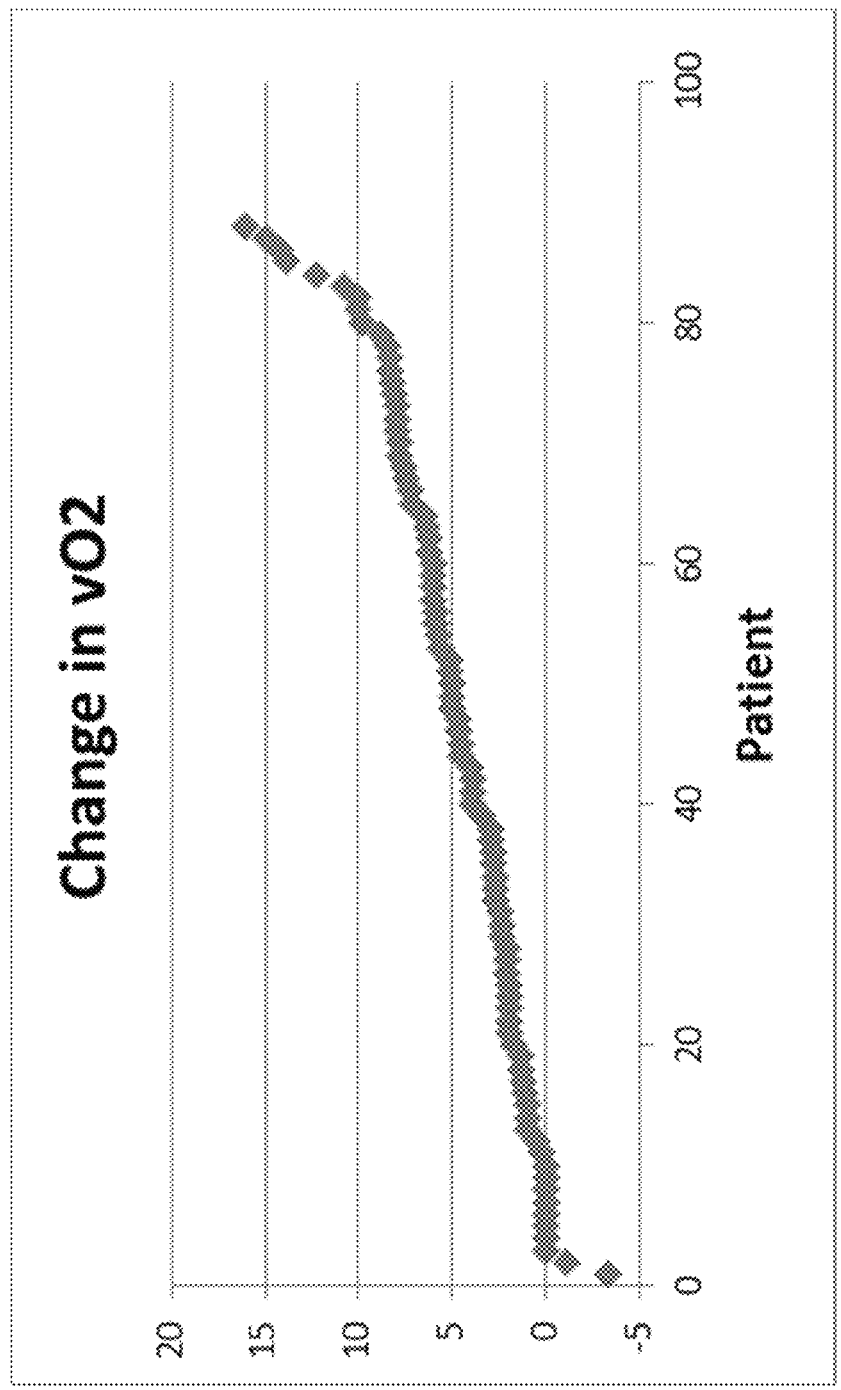
FIG. 35 illustrates the change in VO2, according to one embodiment of the invention.

FIGS. 30-35 are graphical representations of the measured physiological changes in a group of patients over a period of days. FIG. 30 illustrates the overall statistical change in numerous health metrics, including BMI, body fat, trunk fat, RMR and VO2. FIG. 31 illustrates the change in BMI, FIG. 32 illustrates the change in body fat, FIG. 33 illustrates the change in trunk fat, FIG. 34 illustrates the change in resting metabolic rate (RMR) and FIG. 35 illustrates the change in VO2.

VIII. Computer Embodiment

Figure 36:
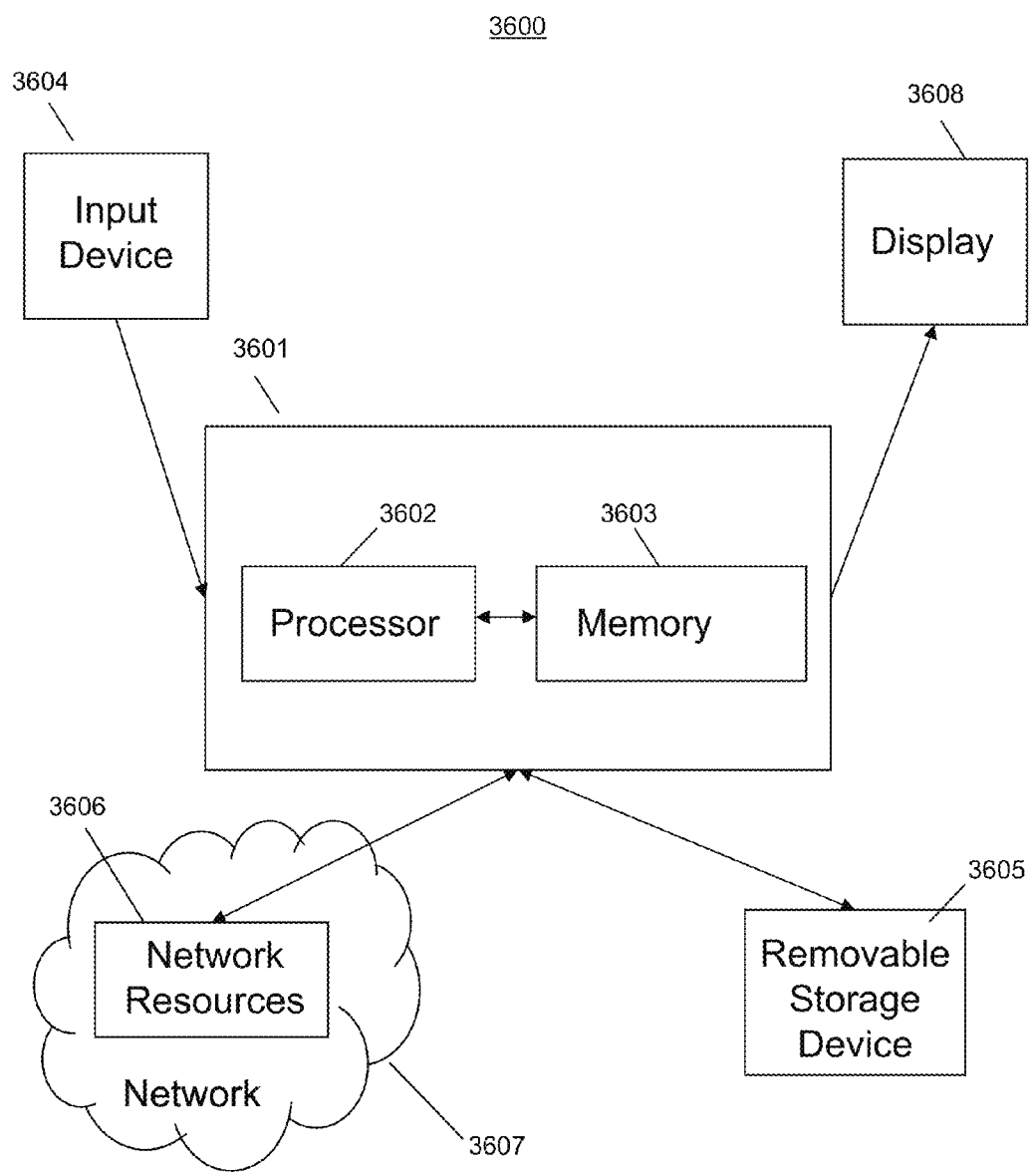
FIG. 36 is a block diagram that illustrates an embodiment of a computer/server system upon which an embodiment of the inventive methodology may be implemented.

FIG. 36 is a block diagram that illustrates an embodiment of a computer/server system 3600 upon which an embodiment of the inventive methodology may be implemented. The system 3600 includes a computer/server platform 3601 including a processor 3602 and memory 3603 which operate to execute instructions, as known to one of skill in the art. The term "computer-readable storage medium" as used herein refers to any tangible medium, such as a disk or semiconductor memory, that participates in providing instructions to processor 3602 for execution. Additionally, the computer platform 3601 receives input from a plurality of input devices 3604, such as a keyboard, mouse, touch device or verbal command. The computer platform 3601 may additionally be connected to a removable storage device 3605, such as a portable hard drive, optical media (CD or DVD), disk media or any other tangible medium from which a computer can read executable code. The computer platform may further be connected to network resources 3606 which connect to the Internet or other components of a local public or private network. The network resources 3606 may provide instructions and data to the computer platform from a remote location on a network 3607. The connections to the network resources 3606 may be via wireless protocols, such as the 802.11 standards, Bluetooth® or cellular protocols, or via physical transmission media, such as cables or fiber optics. The network resources may include storage devices for storing data and executable instructions at a location separate from the computer platform 3601. The computer interacts with a display 3608 to output data and other information to a user, as well as to request additional instructions and input from the user. The display 3608 may therefore further act as an input device 3604 for interacting with a user.

The above description of disclosed embodiments is provided to enable any person skilled in the art to make or use the invention. Various modifications to the embodiments will be readily apparent to those skilled in the art, the generic principals defined herein can be applied to other embodiments without departing from spirit or scope of the invention. Thus, the invention is not intended to be limited to the embodiments shown herein but is to be accorded the widest scope consistent with the principals and novel features disclosed herein.

The invention claimed is:

1. A method for implementing personalized health and wellness programs, comprising the steps of:
   receiving health data pertaining to a user;
   determining a group of health profiles with aggregated data that correlates to the health data pertaining to the user;
   assigning, from the group of health profiles, a user health profile to the user based on the received health data;
   selecting a health and wellness program for the user based on the user health profile, wherein the health and wellness program comprises at least an intervention based on performance of the group of health profiles;
   displaying an interactive Graphical User Interface (GUI) of the health and wellness program pertaining to the user and the aggregated data for the group of health profiles;
   updating the user health profile based on user activity pertaining to the user's participation in the health and wellness program from one or more wireless health devices, wherein the user activity includes tracking metrics of the user's participation in the intervention and a clinical assessment;
   adjusting the group of health profiles to correlate to the updated user health profile; and
   updating the health and wellness program for the user based on the adjusted group of health profiles.

2. The method of claim 1, wherein the health data is at least one of:
   medical history, genetic data, nutrition data, fitness data and environmental data.

3. The method of claim 2, wherein the health data includes an oxygen consumption (VO2) level, resting metabolic rate (RMR), amount of visceral fat, amount of body fat and posture.

4. The method of claim 3, further comprising transmitting notifications to the user regarding the user's participation in the health and wellness program, wherein the notifications are selected based on the user health profile.

5. The method of claim 4, further comprising transmitting messages to the user regarding the user's participation in the health and wellness program, wherein the messages are selected based on the user health profile.

6. The method of claim 5, wherein the messages are created by an administrator or healthcare provider who supervises the user's participation in the health and wellness program.

7. The method of claim 1, further comprising displaying historical health data based on a previous user assessment for comparison with a new assessment.

8. The method of claim 1, further comprising receiving user activity information pertaining to the user's participation in the health and wellness program from an application on a portable electronic device.

9. The method of claim 1, further comprising providing points and rewards for aspects of the user's participation in the health and wellness program.

10. The method of claim 1, further comprising providing recommendations to users participating in the health and fitness program based on previously-selected user activities.

11. An interactive graphical user interface (GUI) for developing and implementing personalized health and wellness programs, comprising a dashboard server comprising a processor which is configured to perform the steps of:
    displaying health data pertaining to a user;
    displaying aggregated data for a group of health profiles that correlates to the health data pertaining to the user and an assigned user health profile based on the group of health profiles;
    displaying a health and wellness program for the user based on the user health profile, wherein the health and wellness program comprises at least an intervention based on performance of the group of health profiles, wherein displaying the health and wellness program includes displaying an interactive GUI of the health and wellness program pertaining to the user and the aggregated data for the group of health profiles;

updating the user health profile based on user activity pertaining to the user's participation in the health and wellness program from one or more wireless health devices, wherein the user activity includes tracking metrics of the user's participation in the intervention and a clinical assessment;

adjusting the group of health profiles to correlate to the updated user health profile; and updating the health and wellness program for the user based on the adjusted group of health profiles.

12. The system of claim 11, wherein the health data is at least one of:

medical history, genetic data, nutrition data, fitness data and environmental data.

13. The system of claim 12, wherein the health data includes an oxygen consumption (VO2) level, resting metabolic rate (RMR), amount of visceral fat, amount of body fat and posture.

14. The system of claim 13, wherein the dashboard server sends notifications to the user regarding the user's participation in the health and wellness program.

15. The system of claim 14, wherein the dashboard server transmits messages to the user regarding the user's participation in the health and wellness program.

16. The system of claim 15, wherein the messages are created by an administrator or healthcare provider who supervises the user's participation in the health and wellness program.

17. The system of claim 11, wherein the interactive GUI displays historical health data based on a previous user assessment for comparison with a new assessment.

18. The system of claim 11, wherein the dashboard server receives user activity pertaining to the user's participation in the health and wellness program from an application on a portable electronic device.

19. The system of claim 11, wherein the interactive GUI displays points and rewards for aspects of the user's participation in the health and wellness program.

20. The system of claim 11, wherein the interactive GUI displays recommendations to users participating in the health and fitness program based on previously-selected user activities.

21. The method of claim 1, wherein the interested party other than the user is a healthcare professional responsible for the user's health.

22. The method of claim 1, wherein the interested party other than the user is a corporate wellness administrator set up to monitor the user's progress toward specific health goals.

23. The system of claim 11, wherein the interactive GUI is configured as an interactive dashboard.

24. The method of claim 8, wherein the information provided by the interested party at the second destination relates to a change to a new user health profile based on the user activity information, the new user health profile indicating defining a health and wellness program and notifications and messages to be provided to the user.

* * * * *